(12) United States Patent
Barisani-Asenbauer et al.

(10) Patent No.: US 10,709,778 B2
(45) Date of Patent: Jul. 14, 2020

(54) VACCINE FORMULATION FOR OCULAR IMMUNIZATION

(71) Applicant: Medizinische Universität Wien, Vienna (AT)

(72) Inventors: Talin Barisani-Asenbauer, Vienna (AT); Aleksandra Inic-Kanada, Vienna (AT)

(73) Assignee: MEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 14/786,155

(22) PCT Filed: Apr. 24, 2014

(86) PCT No.: PCT/EP2014/058390
§ 371 (c)(1),
(2) Date: Oct. 21, 2015

(87) PCT Pub. No.: WO2014/174039
PCT Pub. Date: Oct. 30, 2014

(65) Prior Publication Data
US 2016/0067324 A1 Mar. 10, 2016

(30) Foreign Application Priority Data

Apr. 24, 2013 (EP) .................... 13165103

(51) Int. Cl.
*A61K 39/08* (2006.01)
*A61K 39/39* (2006.01)
(Continued)

(52) U.S. Cl.
CPC ............ *A61K 39/08* (2013.01); *A61K 9/0048* (2013.01); *A61K 31/7052* (2013.01);
(Continued)

(58) Field of Classification Search
CPC ...... A61K 9/0019; A61K 31/00; A61K 35/74; A61K 38/00; A61K 38/164; A61K 39/00;
(Continued)

(56) References Cited

U.S. PATENT DOCUMENTS

2003/0082232 A1* 5/2003 Lee ..................... A61F 2/28
424/484
2004/0170640 A1* 9/2004 Gerber ................ A61K 39/245
424/184.1

(Continued)

FOREIGN PATENT DOCUMENTS

| WO | WO-2007125566 A2 * | 11/2007 | ........... A61K 9/0048 |
| WO | WO 2009/014382 * | 1/2009 | ........... A61K 39/395 |
| WO | WO-2010026239 A1 * | 3/2010 | ............. A61K 39/39 |

OTHER PUBLICATIONS

Barisani-Asenbauer et al., (Acta Ophthalmologica. vol. 90, No Issue Supplement s249, 2844, Aug. 6, 2012).*
(Continued)

*Primary Examiner* — Jana A Hines
(74) *Attorney, Agent, or Firm* — Loza & Loza, LLP; Michael F. Fedrick

(57) ABSTRACT

The present invention relates generally to the field of ocular therapeutics and the development thereof for use in humans and animals including mammals and birds. More particularly, it relates to subunit vaccines that are effective against pathogens causing infections thereof for use in humans and animals including mammals and birds. The present invention specifically provides a novel vaccine formulation suitable for ocular immunization comprising a subunit vaccine antigen in an amount to provoke a protective immune response and at least two adjuvants of which one is corpuscular. It further provides a method for inducing a local and systemic immune response and methods for preventing (Continued)

Figure 1:
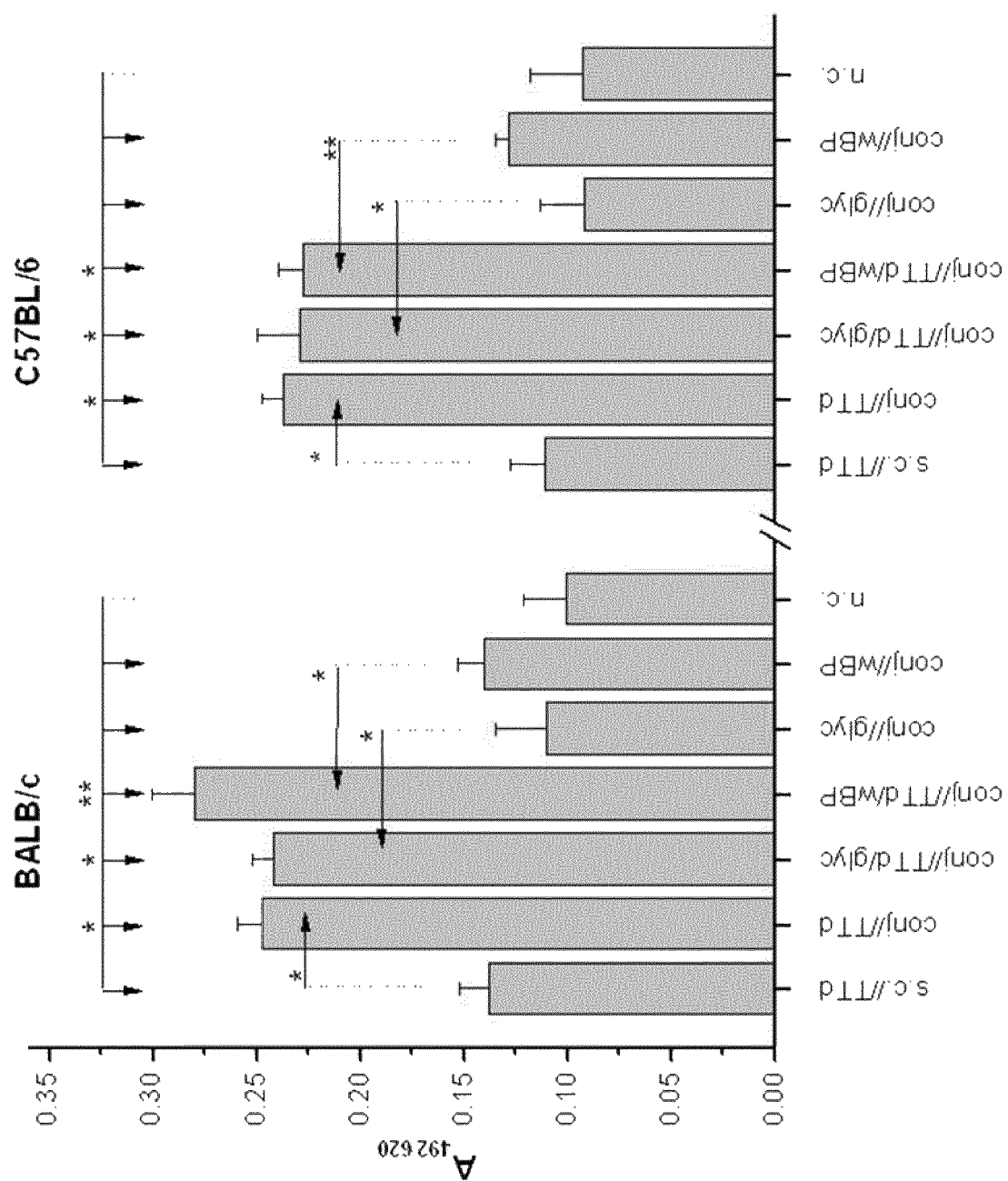

recurrence of ocular infections and/or modulates the occurrence and/or severity of sequels.

15 Claims, 15 Drawing Sheets

(51) Int. Cl.
  *A61K 9/00*  (2006.01)
  *A61K 31/7052*  (2006.01)
  *A61K 47/06*  (2006.01)
  *A61K 39/00*  (2006.01)

(52) U.S. Cl.
  CPC .............. *A61K 39/39* (2013.01); *A61K 47/06* (2013.01); *A61K 2039/54* (2013.01); *A61K 2039/545* (2013.01); *A61K 2039/55583* (2013.01); *A61K 2039/55594* (2013.01); *A61K 2039/6006* (2013.01); *A61K 2039/6087* (2013.01)

(58) Field of Classification Search
  CPC ........ A61K 39/39; A61K 39/40; A61K 39/02; A61K 39/55555; A61K 39/55505; A61K 2300/00; A61K 2039/55511; A61K 2039/58; A61K 39/35; A61K 9/14; A61K 9/20; A61K 9/48; A61K 39/36; A61K 9/02; A61K 9/08; A61K 9/107; A61K 9/16; A61K 39/002; A61K 39/12; A61K 39/245; A61K 47/08; A61K 47/16; A61K 47/46; A61P 37/02; A61P 37/04; A61P 37/06; A61P 37/08; A61P 1/04; B82Y 5/00
  USPC ................... 424/184.1, 275.1, 400, 464, 489
  See application file for complete search history.

(56) References Cited

U.S. PATENT DOCUMENTS

2011/0150987 A1* 6/2011 Saint-Lu ................ A61K 9/006
                   424/451
2011/0229556 A1* 9/2011 Irvine ................... A61K 39/385
                   424/450

OTHER PUBLICATIONS

Baudner et al., (Vaccine. 2003. vol. 21Issue 25-26:3837-3844).*
Martins et al., (J of Controlled Release, 2012. vol. 162(3):553-560).*
Editor Gupta et al. Drugs and the Pharmaceutical Science. vol. 159. Nanoparticle Technology for Drug Delivery. Published 2006. New York, NY. Chapter 11. Nanoparticles for Ocular Drug Delivery. Amrite and Kompella. pp. 319-353.*
Quintillo et al., ( Vaccine. 2009. 27(31): 4219-24).*
Licciardi et al., (Discovery Medicine. Dec. 2011. 12(67):525-533).*
Ludwig (Advanced Drug Delivery Reviews. vol. 57. Issue 11. Nov. 2005: 1595-1639).*
Seo et al., ( J. of Immunol. Sep. 2010, 185(6): 3610-3619) (Year: 2010).*
Fujkuyama et al. (Expert Rev Vaccines. Mar. 2012; 11(3):367-379). (Year: 2012).*
Muhammad et al, "Bacterial ghosts as carriers of protein subunit and DNA-encoded antigens for vaccine applications", Expert Rev. Vaccines, 2012, 97-116.
Islam et al, "Design and application of chitosan microspheres as oral and nasal vaccine carriers: an updated review" Int. J.Nanomed., 2012, 7, 6077-6093.
Bal et al, "Adjuvanted, antigen loaded N-trimethyl chitosan nanoparticles for nasal and intradermal vaccination: Adjuvant- and site-dependent immunogenicity in mice", European Journal of Pharmaceutical Sciences, vol. 45, No. 4, 2012, pp. 475-781.
Barisani-Asenbauer et al., "Immune responses to model antigen elicited by immunization via conjunctive associated lymphoid tissue", Acta Ophthalmologica, 2012, 90, Issue Suppl. s249, 2844, XP-002712570.
Barisani-Asenbauer et al., "The Ocular Conjunctiva as a Mucosal Immunization Route: A Profile of the Immune Response to the Model Antigen Tetanus Toxoid", Plos One, vol. 8, No. 4, E60682, 2013, pp. 1-11, XP-002712572.
Baudner et al, "The concomitant use of the LTK63 mucosal adjuvant and of the chitosan-based delivery system enhances the immunogenicity and efficacy of intransasally administered vaccines", Vaccine, vol. 21, No. 25-26, 2003, pp. 3837-3844.
Blake et al, "Cost-Effectiveness Analysis of Screening Adolescent Males for Chlamydia on Admission to Detention", Sex.Transm.Dis., 2004, 31(2), 85-95.
Chandler et al, "Immunologic Defense Mechanisms of the Ocular Surface", Ophthalmology, 1983, 90, 585-591.
Da Costa Martins et al., "Conjunctival vaccination against Brucella ovis in mice with mannosylated nanoparticles", J.Controlled Disease, 2012, 162, 553-560.
Eko et al, "Development of a Chlamydia trachomatis bacterial ghost vaccine to tight human blindness", Human Vaccines, 2008, 4:3, 176-183.
Holmgren et al, "Mucosal immunity and vaccines", Nat.Med, 2005, 11(4), 45-53.
Holmgren et al, "Vaccines against mucosal infections", Curr Opin. Immunol., 2012, 24(3), 343-53.
Kageyama et al., "Ocular defense mechanisms with special reference to the demonstration and functional morphology of the conjunctiva-associated lymphoid tissue in Japanese monkeys", Arch. Histol. Cytol., 2006, 69(5), 311-322.
Knop et al, "The role of eye-associated lymphoid tissue in corneal immunie protection" J. Anat., 2005, 206, 271-285.
Kudela et al, "Bacterial Ghosts as antigen and drug delivery system for ocular surface diseases: Effective Internalization of Bacterial Ghosts by human conjunctival epithelial cells", J. Biotechnol., 2011, 153, 167-175.
Leung et al, "Prevalence of Ocular Surface Disease in Glaucoma Patients", J. Glaucoma, 2008,17(5):350-355.
Lim et al, "Patterns of regional head and neck lymph node metastasis in primary conjunctival malignant melanoma" Br. J.Ophthalmol., 2006, 90, 1468-1471.
Okada et al, "Craniofacial Mucosal Immune System: Importance of Its Unique Organogenesis and Function in the Development of a Mucosal Vaccine", Adv. Otorhinolaryngol., 2011, 72:31-36, Epub Aug. 18, 2011.
Perrie et al, "Vaccine adjuvant systems: Enhancing the efficacy of sub-unit protein antigens", Int.J.Pharm., 2008, 8, 364(2), 272-280.
Shen et al, "Chlamydia pneumoniae infection, complement factor H variants and age-related macular degeneration", Br.J.Ophthalmol. ,2009, 93(3), 405-408.
Steven et al, "Conjunctiva-Associated Lymphoid Tissue—Current Knowledge, Animal Models and Experimental Prospects", Ophthalmic Res., 2009, 42(1), 2-8.
Vanrompay et al, "Chlamydophila psittaci Transmission from Pet Birds to Humans", Emerg.Infect.Dis., 2007, 1108-1110.
Walcher et al, "Bacterial ghosts as a delivery system for zona pellucida-2 fertility control vaccines for brushtail possums (*Trichosurus vulpecula*)" Vaccine, 2008, 26, 6832-6838.
Watson et al, "Role of Chlamydia pneumoniae in atherosclerosis", ClinSci., 2008, 114(8), 509-531.
International Search Report for PCT/EP14/58390 dated Aug. 6, 2014; 14 pages.
Written Opinion for PCT/EP14/58390 dated Aug. 6, 2014, 8 pages.
International Preliminary Report on Patentability for PCT/EP14/58390 dated Oct. 27, 2015; 8 pages.
Extended European Search Report for EP13165103.6 dated Oct. 11, 2013; 8 pages.
Alonso, M.J. et al. "The potential of chitosan in ocular drug delivery", J of Pharmacy and Pharmaco vol. 55, No. 11, Nov. 1, 2003, pp. 1451-1463.

(56) References Cited

OTHER PUBLICATIONS

Hosoya, K.I. et al. "Roles of conjunctiva in ocular drug delivery: a review of conjunctival transport mechanisms and their regulation", European J of Pharmaceutics and Biopharmaceutics, vol. 60, No. 2, Jul. 2, 2005, pp. 227-240.

Krishna, Sailaja et al. "Chitosan nanoparticles as a drug delivery system", Research Journal of Pharmaceutical, Biological, and Chemical Sciences, vol. 1, No. 3, 2010; pp. 474-484.

Office Action for European Patent Application No. 14723025.4 dated Aug. 14, 2019; 9 pages.

* cited by examiner

A) Chitosan only

B) Corpuscular adjuvants of bacterial origin only

C) Chitosan and corpuscular adjuvants of bacterial origin at 30min

VACCINE FORMULATION FOR OCULAR IMMUNIZATION

CROSS-REFERENCE TO RELATED APPLICATIONS

This application is the U.S. national stage of International Patent Application No. PCT/EP2014/058390, filed on Apr. 24, 2014 and entitled NOVEL VACCINE FORMULATION FOR OCULAR IMMUNIZATION, which claims the benefit of priority under 35 U.S.C. § 119 from European Patent Application No. 13165103.6, filed Apr. 24, 2014. The disclosures of the foregoing applications are incorporated herein by reference in their entirety.

FIELD OF THE INVENTION

The present invention relates generally to the field of ocular therapeutics and the development thereof for use in subjects, including mammals, humans and birds. More particularly, it relates to subunit antigen vaccines that are effective against pathogens causing infections thereof for use in subjects.

The present invention specifically provides a novel vaccine formulation suitable for ocular immunization of a subject comprising a subunit vaccine antigen in an amount to provoke a protective immune response and two adjuvants of which one is corpuscular. It further provides a method for inducing a local and systemic immune response and methods for preventing recurrence of ocular infections and/or its sequels.

BACKGROUND OF THE INVENTION

Ocular surface diseases, especially ocular infections, encompass a plethora of pathologies with overlapping conditions leading to common sequels: dysfunction of the ocular tear film and/or the integrity of the ocular surface. The ocular surface is richly innervated by sensory nerves, therefore, any stimulus that affects these tissues can lead to a variety of symptoms. These range from mild discomfort to grittiness, foreign body sensation, irritation, and dryness affecting the quality of life of millions. Furthermore inflammation can cause damage to the various structures of the ocular surface: i.e. scarring of tissues underlying the conjunctival epithelium and destruction of the Becher-cells leading to dry eyes and/or causing irregularity of the corneal surface that might result in glare. In severe cases, where the condition is chronic with surface damage, it might lead to mild to profound decreases in vision as seen in severe dry eyes syndromes, vernal keratoconjunctivitis or infectious diseases as trachoma.

Specifically, trachoma is one of the neglected tropical diseases and remains the world's leading infectious cause of blindness. It is estimated that more than 500 million people are at high risk of infection, over 140 million are infected. It affects clinically about 21.4 million people of whom about 2.2 million are visually impaired and 1.2 million are blind. It is responsible, at present, for more than 3% of the world's blindness but the number keeps changing due to the effect of socio-economic development and current control programmes for this disease.

*Chlamydia trachomatis* also causes morbidity worldwide through infections manifesting in the genitourinary tract causing cervicitis and/or urethritis. In fact these infections are the most common form of bacterial sexually transmitted diseases (STDs), placing enormous socioeconomic burden on societies (Blake et al, Sex. Transm. Dis., 2004, 31(2), 85-95). *Chlamydia pneumoniae* (now classified as *Chlamydophila pneumoniae*) was first associated with mild respiratory infections but has recently emerged as a relevant pathogen associated with atherosclerosis, adult-onset asthma, macular degeneration and certain other chronic diseases (Watson et al, Clin. Sci., 2008, 114(8), 509-31; Shen et al, Br. J. Ophthalmol., 2009, 93(3), 405-8). The zoonotic *Chlamydophila psittaci* constitutes an occupational hazard for workers in the poultry and farming industry, and persons exposed to infected avian species (Vanrompay et al, Emerg. Infect. Dis., 2007, 1108-10).

Although affecting the majority of individuals with ocular symptoms, ocular surface diseases, especially ocular surface infections, are globally under-recognized and neglected. This is also reflected in drug development as most of the topical drugs used in the management of ocular surface diseases are optimized for intraocular delivery meaning that they are not developed to reach the ocular surface but to overcome it in its barrier function. Drug penetration into the anterior chamber is improved by increasing lipophilicity for better transcellular transport and by the use of enhancers like actin filament inhibitors, surfactants, and bile salts to open tight junctions for better paracellular absorption through the ocular surface. The use of these drugs contributes inevitably on the long run to more ocular surface dysfunction. Similar findings are also seen in chronic usage of topical therapeutics prescribed for other ocular conditions as glaucoma where the prevalence of ocular surface disease in patients with glaucoma is fairly common. Leung et al. reported that half of their patients being treated for glaucoma had ocular surface disease at least in one eye seeing as exacerbation of underlying ocular surface disease secondary to medications (Leung E W et al., J. Glaucoma. 2008 August; 17(5):350-5. doi: 10.1097/IJG.0b013e31815c5f4f.). On the other hand, anti-inflammatory therapy of the ocular surface often leads to adverse events in the intraocular compartment, too. Secondary glaucoma and cataract formation are common in chronic topical steroid usages.

The conjunctiva and its underlying structures are now accepted as a part of the mucosa-associated lymphoid tissue (MALT) and are annotated as the conjunctiva-associated lymphoid tissue (CALT) or the eye-associated lymphoid tissue (EALT; Nelson D. et al., The conjunctiva: anatomy and physiology. In Cornea (3rd edition, vol 1, eds.: Krachmer J H, Mannis M J, Holland E J) 2010: 25-32, Mosby, Elsevier).

CALT has the typical components of a physiologically protective mucosal immune system, as it contains diffuse lymphoid tissues and lymphoid follicles that form the efferent and the afferent limbs, respectively, of a lymphoid tissue. Thus, CALT can detect antigens from the ocular surface, present them to lymphoid cells and generate protective effector cells; together, these properties signify the presence of a mucosal immune system at the conjunctiva (Knop E. and Knop N., J. Anat., 2005, 206, 271-285; Chandler J W et al., Ophtalmology, 1983, 90, 585-591). The delivery of vaccines via the conjunctiva would also be an attractive option for mucosal immunization, as eye drops are easily administered, drop-count dosing is feasible, conjunctival inflammation is easily noticeable and, as the conjunctiva is interconnected with the nasal mucosa via the tear ducts, administration of antigens to the conjunctival sac would also drain to reach the nasal-associated lymphoid tissue (NALT). Conjunctival immunization with live attenuated vaccines has been used in veterinary applications and proven an efficient route in many animal models for different infectious diseases (Lim M., et al., Br. J. OPhtalmol., 2006, 90, 1468-1471; Okada K. et al., Adv. Otorhinolaryngol., 2011, 72, 72-31), for example in poultry against Newcastle virus, infectious bursitis virus, chicken herpes virus and turkey herpes virus, in feline viral rhinotracheitis, calicivirus and panleukopeas, and in goats and sheep against *Brucella ovis* (Steven P, Gebert A, Ophthalmic Res., 2009, 42(1), 2-8; Kageyama M. et al., Arch. Histol. Cytol., 2006, 69(5), 311-22).

Barisani-Asenbauer T. et al. (Acta Ophthalmologica, 2012, 90, Issue Suppl. s249, 2844) describe studies, wherein animals are immunized with tetanus toxoid together with inactivated *Bordetella pertussis*.

Ariful Islam M. et al. (Int. J. Nanomed., 2012, 7, 6077-6093) disclose chitosan microspheres for oral or nasal administration of vaccines.

The use of *Brucella ovis* glycoproteins encapsulated in mannosylated nanoparticles of 300 nm size is disclosed by Costa Martins R. et al (J. Controlled Disease, 2012, 162, 553-560).

Walcher P. et al. (Vaccine, 2008, 26, 6832-6838) describe the use of bacterial ghosts for expressing ZP2 polypeptides and their use as fertility control in opossums as facial sprays randomly reaching the nasal and eye area.

Eko F. O. et al. (Human Vaccines, 2008, 4:3, 176-183) also disclose the use of a bacterial ghost vaccine containing *Chlamydia* antigens for the treatment of *Chlamydia trachomatis*.

Abbas, M. (Expert Rev. Vaccines, 2012, 97-116), describes a potential vaccine system using bacterial ghost expressing antigens.

In Kudela P. et al. (J. Biotechnol., 2011, 153, 167-175) bacterial ghosts as antigen and drug delivery system without the use of further adjuvants for ocular surface diseases is described and did not show a cytotoxic effect in the studies. To date, the number of mucosal registered vaccines for human application remains very limited and is principally based on live attenuated pathogens and/or vectors, which contain their own danger signals and mechanisms of mucosal entry (Perrie Y., et al., Int. J. Pharm., 2008, 8, 364(2), 272-80). It is further hampered due to the lack of sufficient overall immune response which provides effective vaccination.

Thus there is still an unmet demand for vaccines which are not only a safe and efficient alternative to live attenuated vaccines but also provide protection at the site of primary infection—the mucosal tissues especially the ocular surface. The development of treatment options targeting the ocular surface would be helpful to reach protection locally and/or reduce the rate of severity of sequels. Optimally a delivery platform is needed that penetrates ocular surface cells with properties that hinders the trans- and paracellular transport into the normal eye on one side (Gukasyan H J et al., Biotechnology: Pharmaceutical Aspects Volume VII, 2008, pp 307-320) and on the other side is safer than live attenuated vaccines.

SHORT DESCRIPTION OF THE INVENTION

The problem is solved by the present invention. The present invention provides a vaccine formulation or preparation suitable for ocular immunization of a subject comprising a subunit vaccine antigen in an amount to provoke a protective immune response in a subject, and at least two adjuvants of which one is corpuscular in nature.

It was surprisingly found by the inventors that subunit vaccines, which are based on purified proteins or carbohydrates, used via conjunctiva are a safe and highly immunogenic alternative to live attenuated vaccines.

Efficient delivery of protein antigens via the conjunctival route of immunization is of remarkable interest in order to both (i) mimic the bacterial infection route pattern and (ii) generate immunity at the site of entry for these microorganisms avoiding all hitches that live-attenuated vaccines could bring along.

According to an embodiment of the invention the antigen is an isolated antigen, specifically a protein or carbohydrate antigen, a protein subunit antigen or a recombinant protein.

According to a further embodiment of the invention the antigen is originating from a pathogen selected from the group consisting of bacteria as *Chlamydia*, Clostridia, *Brucella, Yersinia* or virus, specifically selected from the group consisting of outer membrane protein 2 (OMP2), class I accessible protein 1 (Cap1), cysteine-rich protein A (CrpA), *Chlamydia* polymorphic membrane proteins (Pmps), specifically PmpA to PmpI, *Chlamydia* heat shock protein 60 (HSP60), *Chlamydia* heat shock protein 10 (HSP10), *Chlamydia* protease-like activity factor (CPAF), *Yersinia pseudotuberculosis* (YopD) or a homolog thereof, enolase, arginine binding protein (ArtJ), V-type ATP synthase subunit A (AtpA), peptidyl-prolyl cis-trans isomerase (Mip), glycogen synthase (GIgA), iron binding protein (YtgA), Vtype ATP synthase subunit E (AtpE), type III secretion chaperone (SycD), type III secretion proteins SctC or SctJ, tetanus toxoid, herpes simplex virus, varicella zoster virus or any combinations, fragments or derivatives thereof.

Specifically, the vaccine subunit antigen is originated from *Chlamydia* subunit proteins, specifically omp2, Pmps or any combinations, fragments or derivatives thereof.

According to an embodiment, the formulation may be formulated in single dosage form, which comprises the antigen at a dose ranging between 5 ng to 100 μg, specifically between 50 ng and 90 μg, specifically between 100 ng and 75 μg, specifically between 500 ng to 50 μg.

According to a further embodiment, the inventive formulation comprises an adjuvant that is a biodegradable polymere, preferably the formulation is comprising chitosan.

According to a further embodiment of the invention, the formulation comprises a subunit vaccine antigen together with at least two different adjuvants, specifically at least three, specifically at least four or more different adjuvants of which at least one is corpuscular.

According to a specific embodiment, one of the at least two adjuvants is a polymer.

According to a further embodiment, said polymer is chitosan.

According to an embodiment, the corpuscular adjuvant is a non-pathogenic microbial cell preparation, specifically selected from the group consisting of bacteria, more specifically a preparation of bacterial origin, specifically selected from the group consisting of bacteria, preferably inactivated or attenuated bacteria and/or parts or fragments thereof and/or a corpuscular polymer of a size >300 nm.

In a further embodiment of the invention the subunit antigen is conjugated to a carrier and wherein said carrier specifically is a biodegradable polymer, preferably chitosan, a non-pathogenic microbial cell preparation, preferably selected from the group consisting of bacteria, more preferred a preparation of bacterial origin, preferably selected from the group consisting of bacteria, preferably inactivated or attenuated bacteria and/or parts or fragments thereof.

According to a further embodiment of the invention, the adjuvant or carrier originates from a genus selected from the group consisting of a genus *Bordetella, Lactobacillus, Bifidobacterium* and *Escherichia*, preferably the species *Bordetella pertussis, Lactobacillus* spp., *Bifidobacterum bifidum, Escherichia coli*.

In yet a further embodiment, the adjuvant has a particle size ranging from about 1 nm to 50 µm, specifically from about 5 nm to about 25 µm, specifically from about 10 nm to about 5 µm, specifically from about 100 nm to 5 µm, specifically from about 250 nm to 5 µm, specifically the corpuscular adjuvant size is more than 300 nm.

According to a further embodiment of the invention, the formulation further comprises glycerol, inulin or plant lectins, specifically banana lectin (BanLec-1), and type 2 ribosome-inactivating protein (type 2 RIP), mistletoe lectin I (ML-I), CpG, probiotic bacteriocines, a salt of calcium, iron, or zinc, an insoluble suspension of acylated tyrosine, acylated sugars, cationically, or anionically derivatised polysaccharides, or polyphosphazenes.

In a further embodiment of the invention, the formulation further comprises an antiphlogistic agent, specifically an agent with additional anti-inflammatory/anti-infective properties, specifically azithromycin.

In a further embodiment the antigen and a carrier or an additional adjuvant is provided, wherein the adjuvant is a mixture, an adsorbate or a conjugate.

In a further embodiment the inventive formulation is provided as a kit of parts, comprising
a) a component containing the antigen;
b) a component containing carrier/adjuvants; specifically two or more different adjuvants, specifically one or more corpuscular adjuvants, and optionally
c) means to dispense the formulation.

According to an embodiment of the invention, the formulation comprises as a carrier at least one of a buffer, diluent, encapsulating material or formulation auxiliary.

According to an embodiment of the invention, the formulation is provided as eye drops, spray, aerosol or hydrogel.

The present invention also provides the use of the inventive formulation in treating a subject by active immunotherapy, wherein the formulation is administered to said subject by the ocular or conjunctival route to provoke a protective immune response in the subject.

As a further embodiment, the formulation can be used in preventing recurrence of ocular infections in a subject.

According to a further embodiment, the antigen and the adjuvant are administered separately or simultaneously.

According to a further embodiment the protective immune response induced by the inventive preparation or medicament is a local and systemic one, inducing secretory IgA (SIgA) and IgG specifically recognizing the vaccine antigen.

According to a further embodiment the formulation used is formulated as a vaccine for in vivo administration to the subject in such a way that the individual components of the composition are formulated such that the immunogenicity of individual components is not substantially impaired by other individual components of the composition.

FIGURES

FIG. 1. Levels of TTd-specific SIgA in tear washes from BALB/c and C57BL/6 mice that were immunized according to the assigned protocols. Samples were collected two weeks after the completion of the immunizations and were assayed by ELISA (dilution 1:2). The results are presented as the mean $A_{492/620} \pm SE$ (n=10). The significance of the observed differences was calculated by t-test ($P<0.05^*$, $P<0.005$). The reference group is indicated by a dotted line, and the comparison group is indicated by an arrow.

Figure 2A:
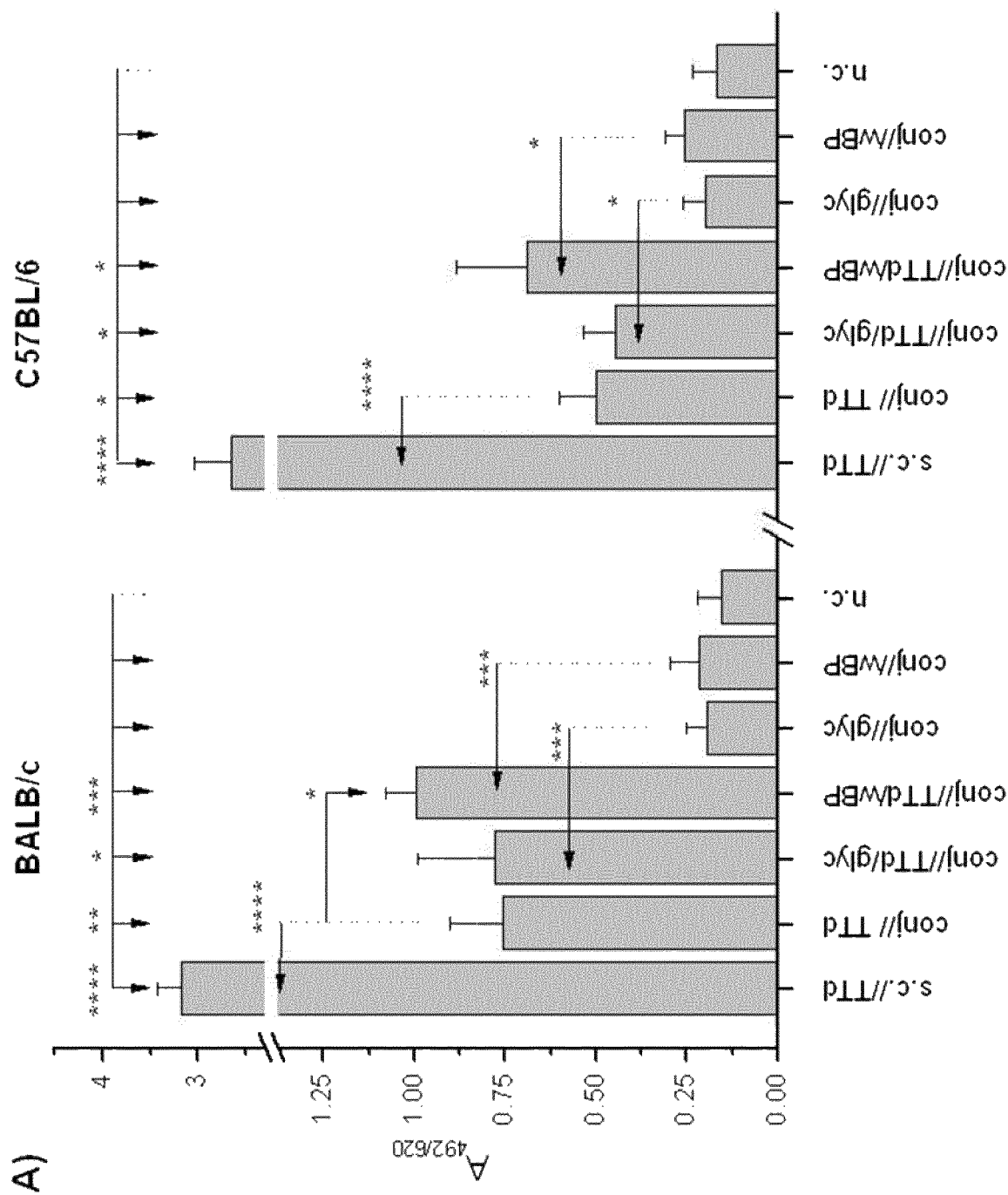
Figure 2B:
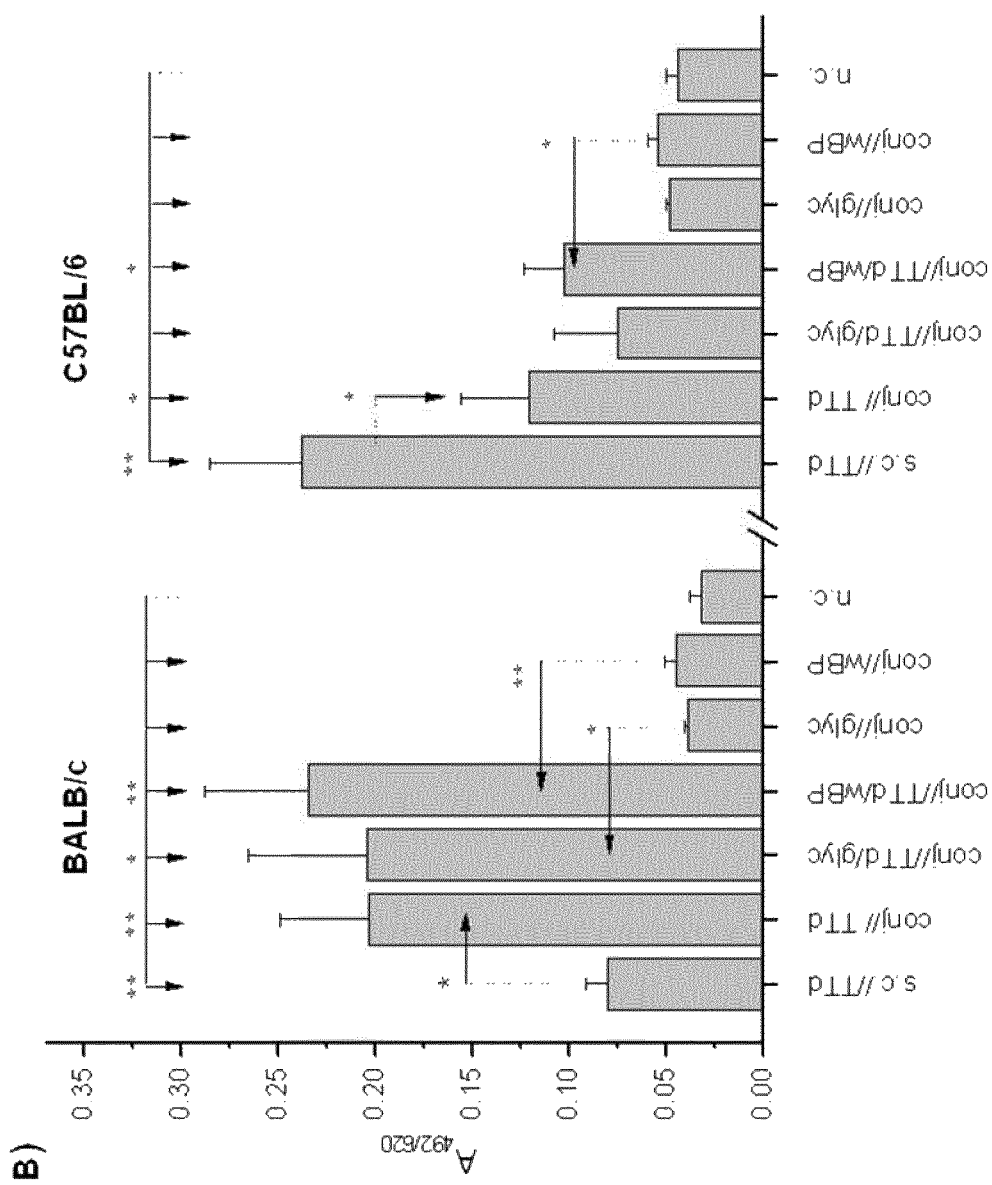

FIG. 2. Levels of TTd-specific IgG (A) and IgA (B) in the sera of BALB/c and C57BL/6 mice immunized according to the assigned protocols. Serum samples were collected two weeks after the completion of the immunizations and were assayed by ELISA (dilution 1:100). The results are presented as the mean $A_{492/620} \pm SE$ (n=10). The significance of the observed differences was calculated by t-test ($P<0.05^*$, $P<0.005^{}$, $P<0.0005^{*}$, $P<0.00005$). The reference group is indicated by a dotted line, and the comparison group is indicated by an arrow.

Figure 3:
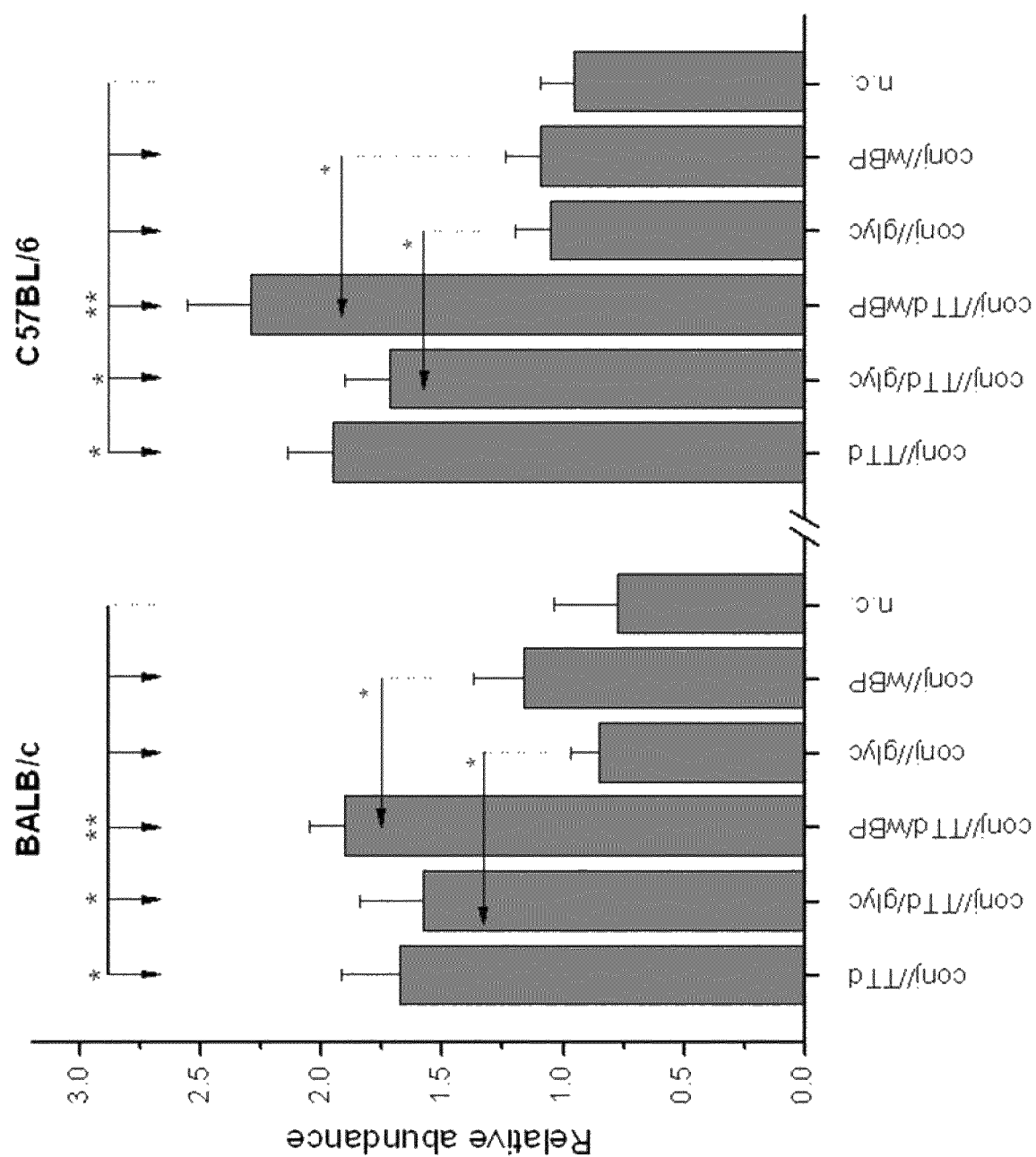

FIG. 3. The relative abundance (RA) of TTd-specific mIgG$^+$ B cells within the total population of mIgG$^+$ B cells in SMLN upon completion of the assigned immunization protocols. The RA of the TTd-specific mIgG$^+$ B cell population was calculated for each mouse. The results are presented as the mean RA±SE for each experimental group of mice (n=5). The statistical significance of the observed differences in TTd-specific mIgG$^+$ B cell pool abundances was determined by t-test ($P<0.05^*$, $P<0.005^{}$, $P<0.0005^{*}$). The reference group is indicated by a dotted line, and the comparison group is indicated by an arrow.

Figure 4:
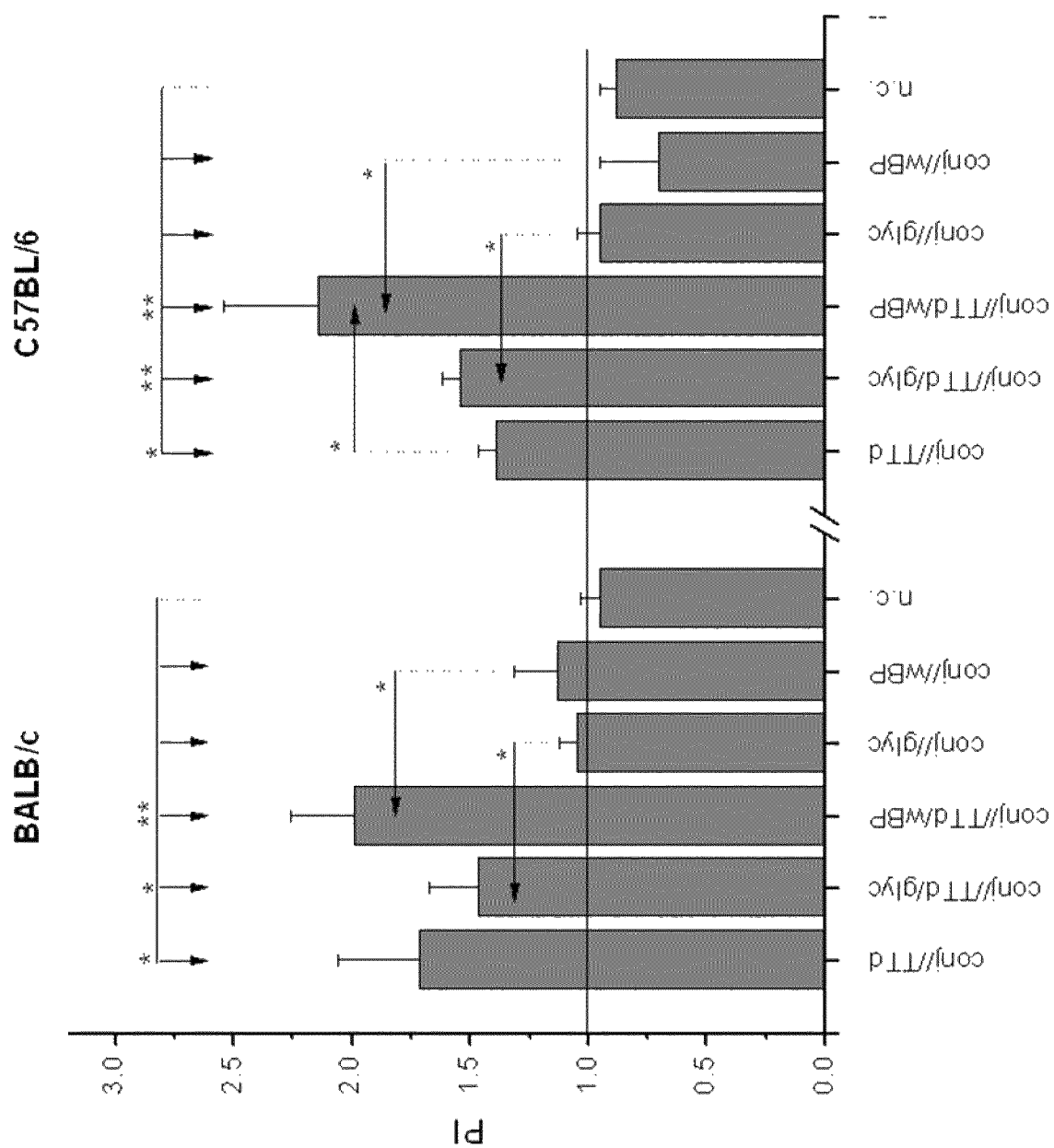
Figure 5A:
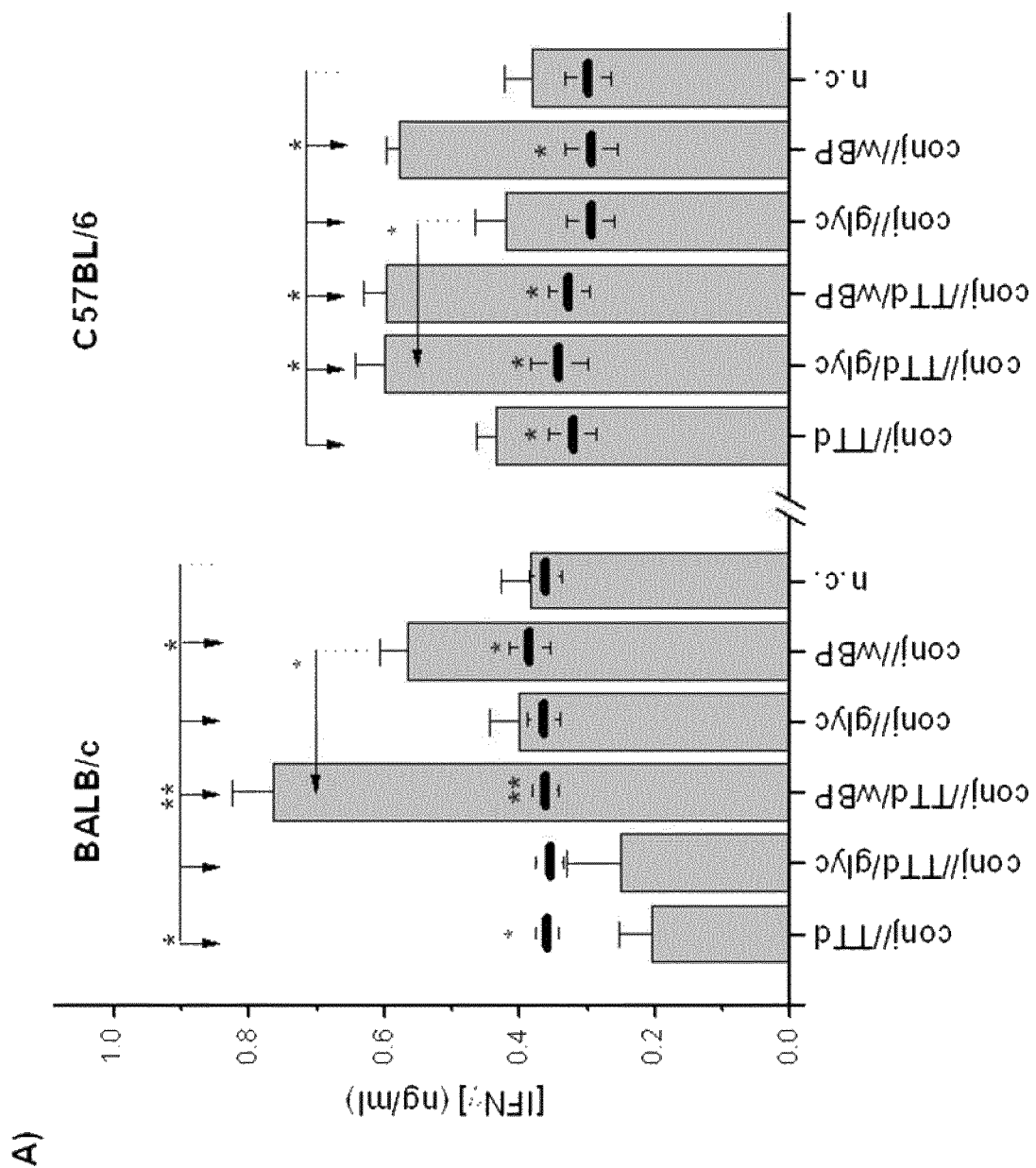
Figure 5B:
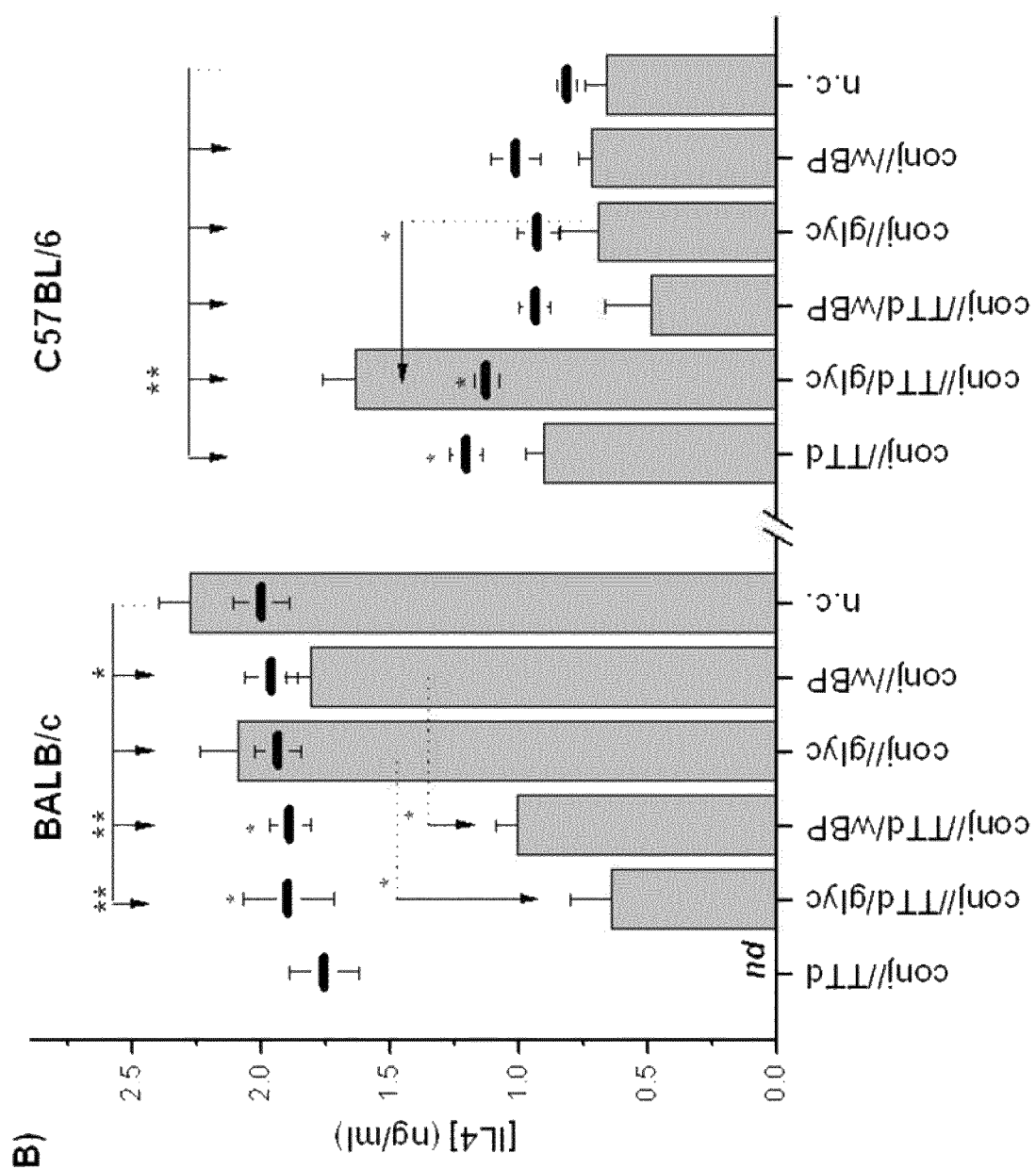
Figure 5C:
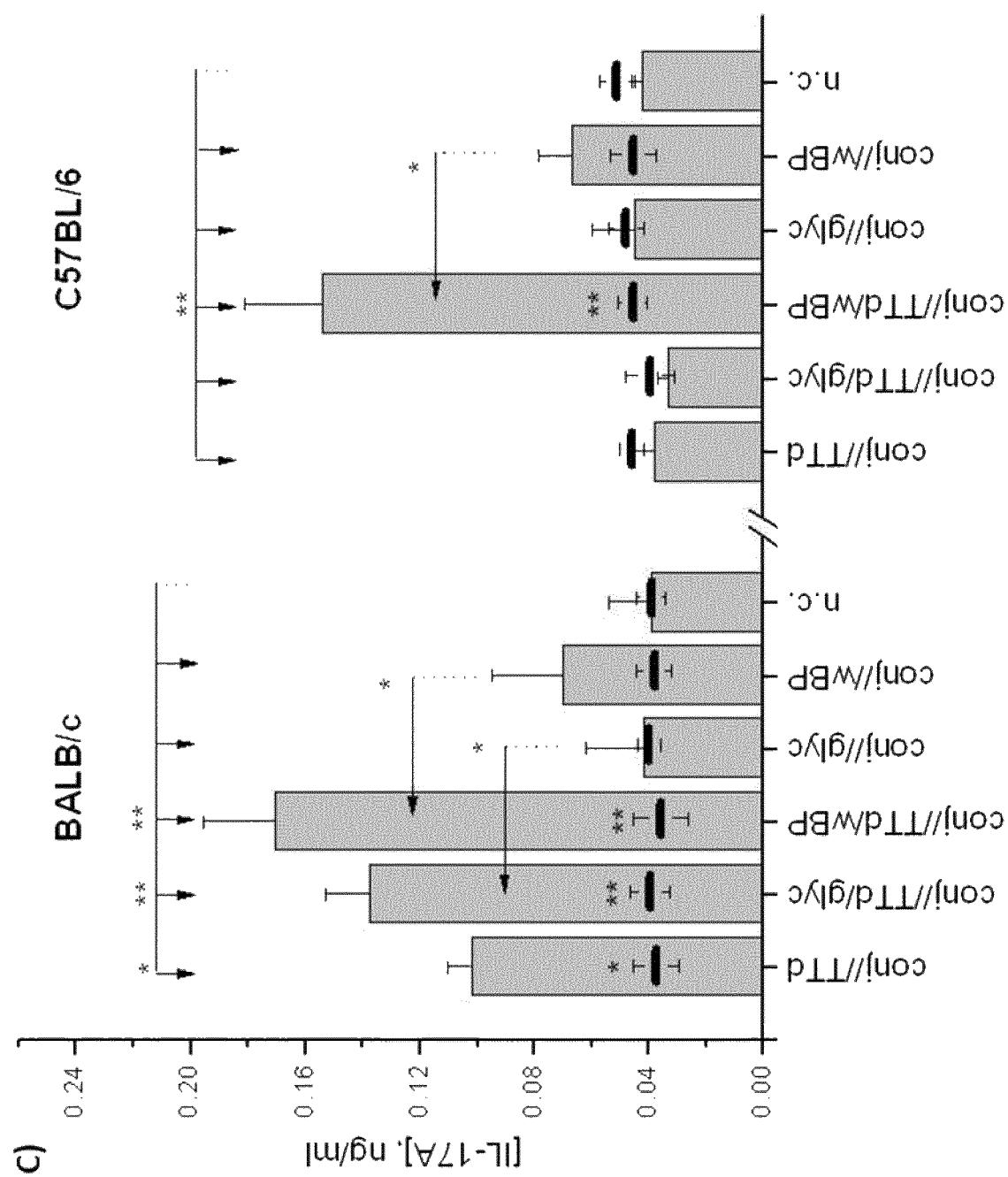
Figure 5D:
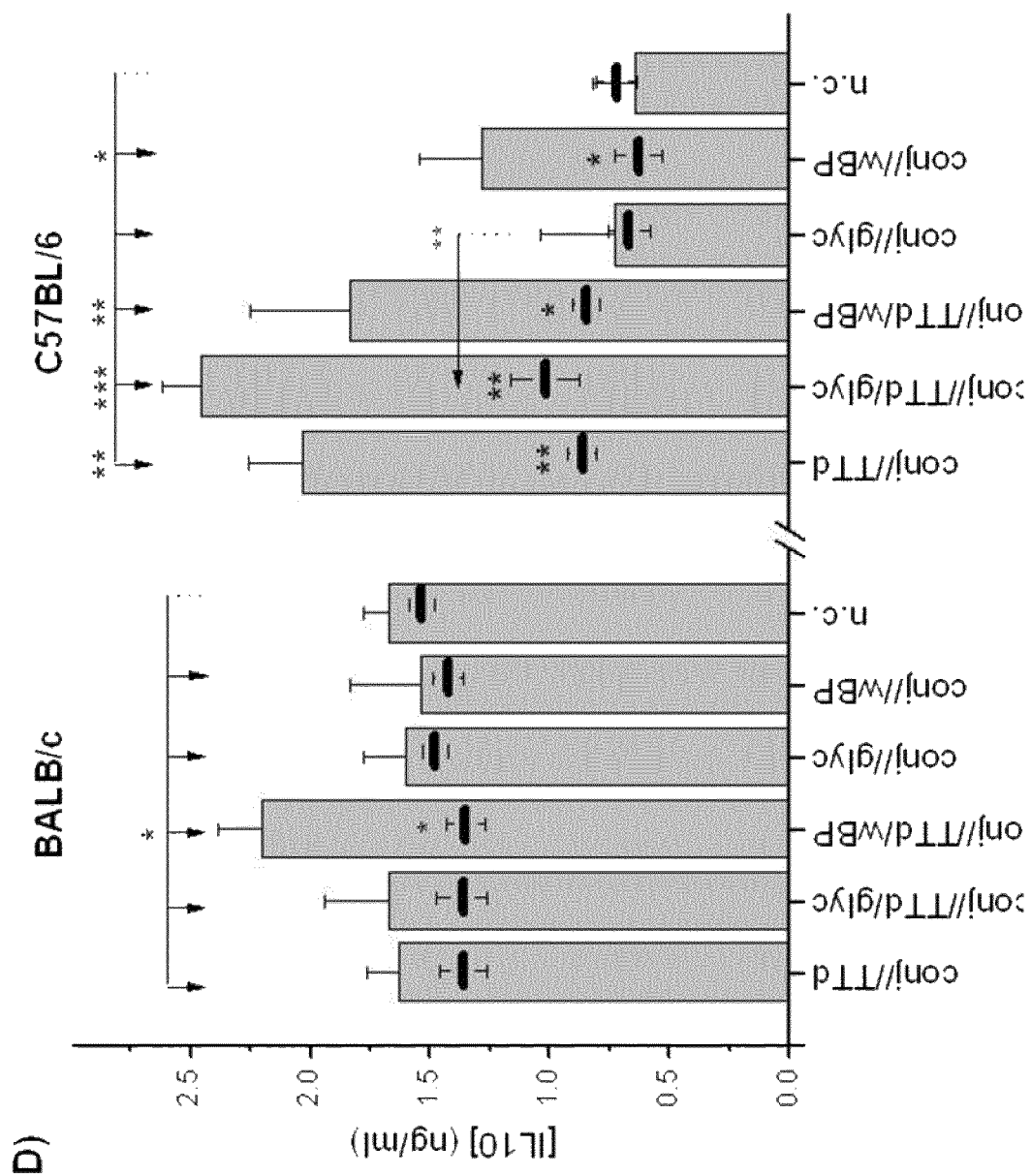

FIG. 4. The proliferation indices (PI) of TTd-stimulated SMLN cells from BALB/c and C57BL/6 mice immunized via the conjunctiva according to the assigned immunization protocol. The numbers of viable SMLN cells were assessed by MTT assay following a 48 h cultivation in 10% FCS/50 µM β-mercaptoethanol/RPMI 1640 medium supplemented or not with TTd (5 µg/ml). PIs were calculated for each mouse. The results are presented as the mean PI±SE for each experimental group (n=10). The statistical significance of the differences in PIs between groups treated according to the assigned protocols was determined by t-test ($P<0.05^*$, $P<0.005^{**}$). The reference group is indicated by a dotted line, and the comparison group is indicated by an arrow.

FIG. 5. Levels of IFNγ (A), IL-4 (B), IL-17A (C) and IL-10 (D) in the supernatants from in vitro TTd-stimulated SMLN cells obtained from age-matched control mice (n.c.) and mice immunized via the conjunctiva according to the assigned protocol (bars). SMLN cells were cultivated at 37° C. in 5% $CO_2$ for 48 h in 10% FCS/RPMI 1640/50 µM β-mercaptoethanol supplemented with 5 µg/ml TTd. The levels of cytokines in the supernatants of corresponding SMLN cells incubated in 10% FCS/RPMI 1640/50 µM β-mercaptoethanol under similar conditions (non-stimulated cells) are indicated by solid lines. The results are presented as the mean concentration±SE (n=10). Concentrations of cytokines in supernatants of TTd-stimulated cultures were compared by t-tests. The reference group is indicated by a dotted line, and the comparison group is indicated by an arrow. A t-test was also used for the comparison of cytokine concentration in supernatants of corresponding non-stimulated and TTd-stimulated cultures, and the statistical significance of the differences is marked next to the solid bar, indicating the level of the cytokine within the non-stimulated culture. The levels of statistical significance are assigned as follows: $P<0.05^*$, $P<0.005^{}$, $P<0.0005^{*}$.

Figure 6:
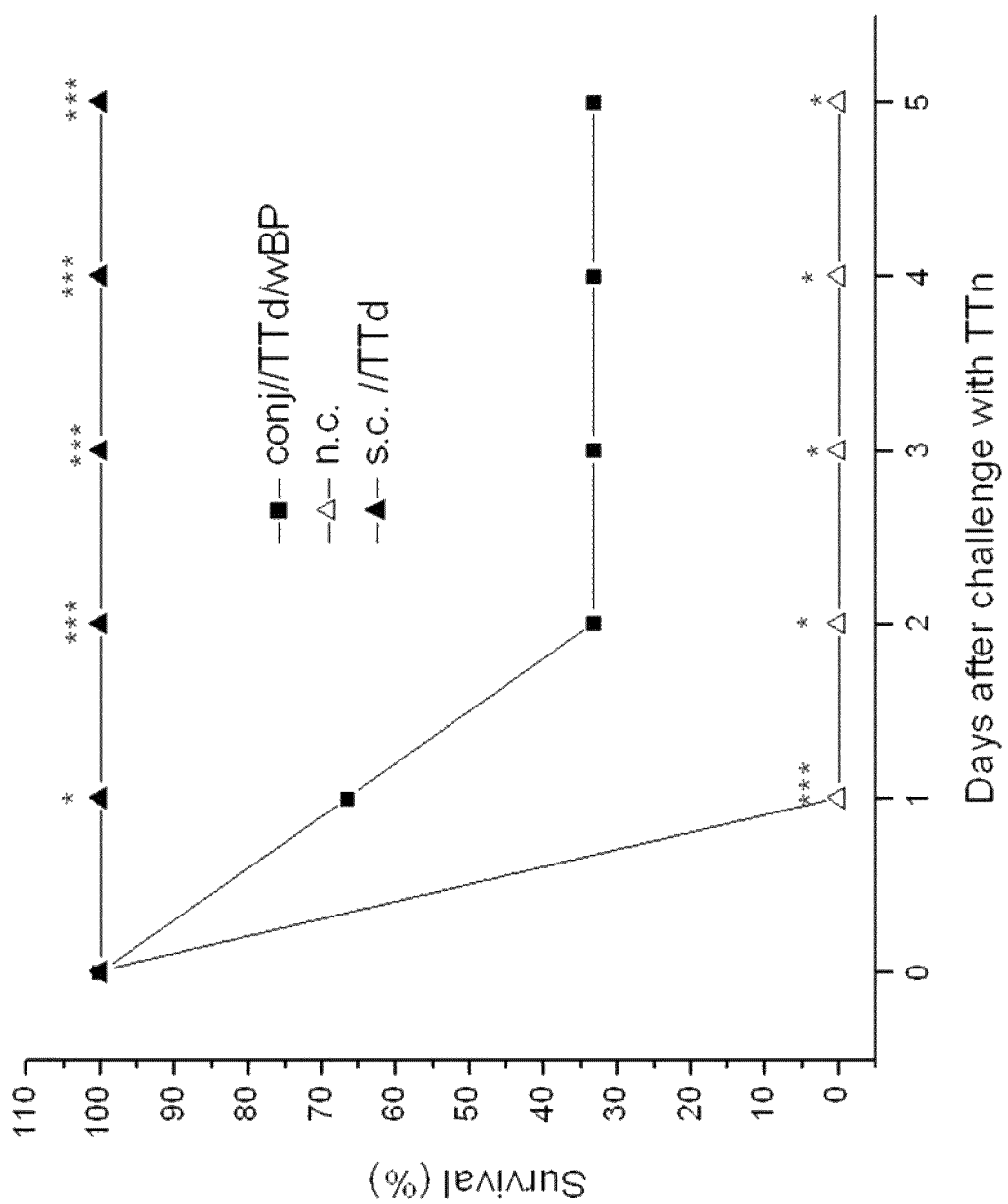

FIG. 6. Survival rate of BALB/c and C57BL/6 mice immunized with TTd subcutaneously (s.c.//TTd), TTd mixed with wBP via the conjunctiva (conj//TTd/wBP) and non-treated age-matched mice (n.c.) upon challenge with tetanus toxin (TTn). Mice were immunized on days 0, 7 and 14 (100 µg TTd per dose) and four weeks after the completion of the specified immunization protocol, mice were challenged by i.p. administration of $2 \times LD_{50}$ of TTn. In both strains, survival rates were the same; hence, a representative plot is provided. Survival rates were monitored daily. The statistical significance of the differences in survival rates between conj//TTd/wBP (reference group) and s.c.//TTd or n.c. groups was determined by t-test (P<0.05*, P<0.005, P<0.0005*). The results are representative of two independent experiments, each comprising 6 mice per group.

Figure 7:
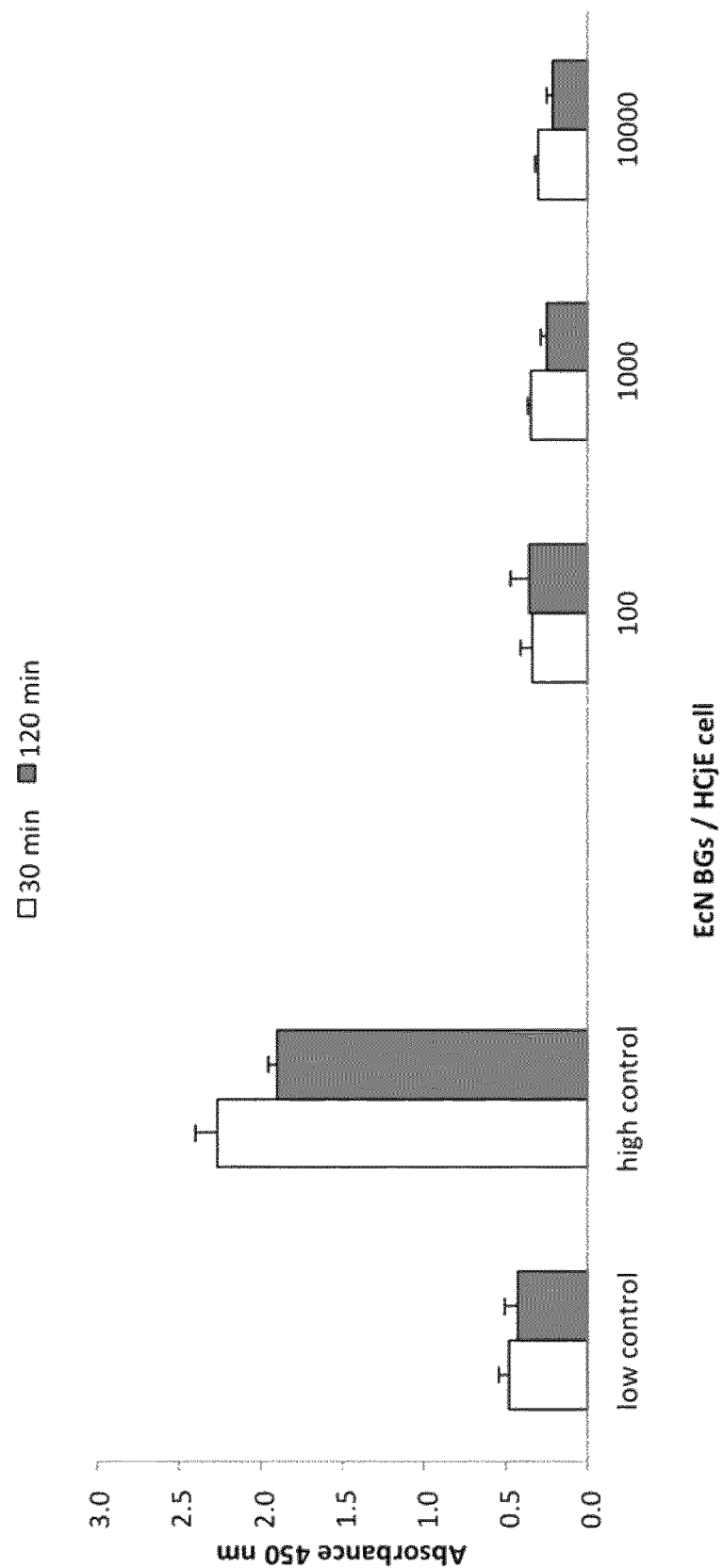

FIG. 7. HCjE cells were seeded onto chamber slides at a density of $2 \times 10^5$ cells/well and incubated at 37° C. overnight. $2 \times 10^8$ of corpuscular adjuvants of bacterial origin labelled with ATTO-390 (Sigma-Aldrich, St. Louis, Mo.) dissolved in boric acid buffer (BAB), 0.05% chitosan-fluorescein isothiocyanate (FITC; Akina, USA) dissolved in BAB, and $2 \times 10^8$ of labelled corpuscular adjuvants of bacterial origin dissolved in 0.05% labelled chitosan were added to separate wells containing HCjE cells for 30 minutes. The cells were washed with PBS, quenched with 0.4% trypan blue for 5 minutes and stained with CellMask plasma membrane stain (2.5 µg/ml; Molecular Probes, Inc., Eugene, Oreg.) for 5 minutes, both at 37° C. Then the cells were fixed with 4% PFA, mounted and examined by epifluorescence microscopy (Zeiss Axiovert 100; Carl Zeiss GmbH, Vienna, Austria).

Figure 8:
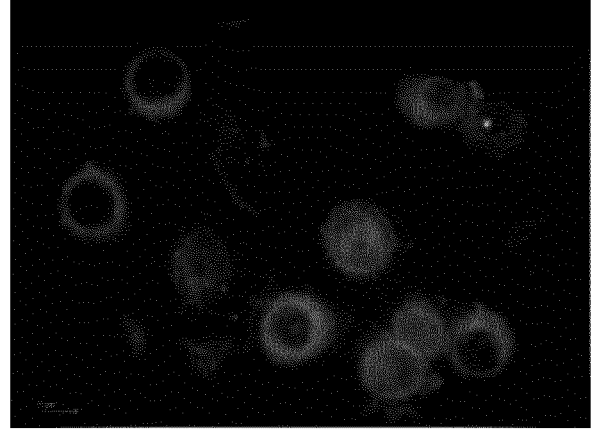
Figure 8:
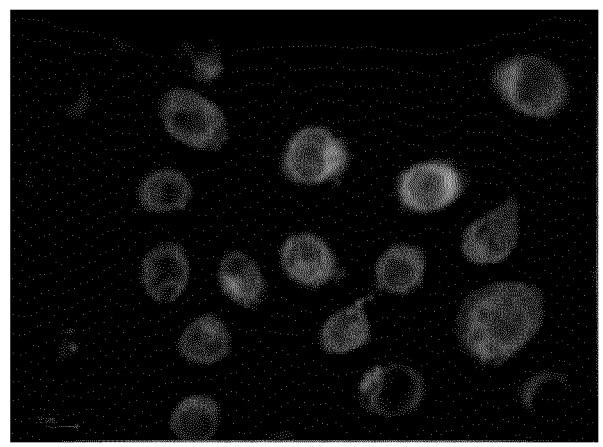
Figure 8:
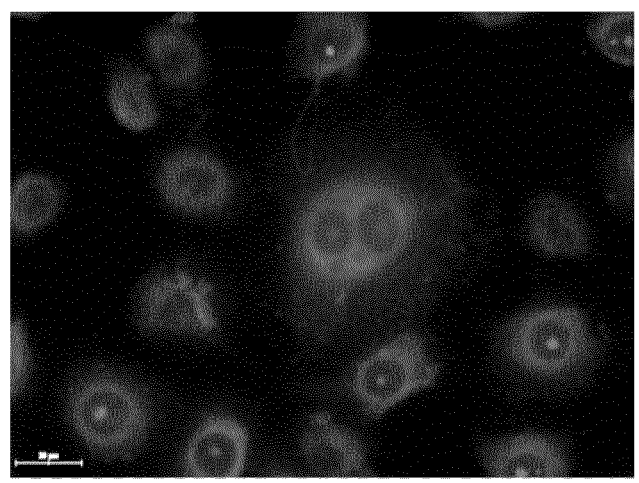

FIG. 8. Internalisation of corpuscular adjuvants of bacterial origin. As demonstrated in previous experiments, corpuscular adjuvants of bacterial origin are readily taken up by the HCjE cells. The addition of chitosan significantly increased the uptake of corpuscular adjuvants of bacterial origin into the HCjE cells.
 a) chitosan only;
 b) corpuscular adjuvants of bacterial origin only;
 c) chitosan and corpuscular adjuvants of bacterial origin at 30 min FIG. 9. Influence of corpuscular adjuvants of bacterial origin on the viability of HCjE cells. Cells were seeded at a density of $4 \times 104$ cells in 96-well plates and incubated with corpuscular adjuvants of bacterial origin at three different MOIs [100, 1000 and 10.000 corpuscular adjuvants of bacterial origin/cell]. Total co-incubation times were 30 min and 120 min under standard conditions (5% $CO_2$/37° C.). LDH release was measured after 30 min, 120 min and 24 h. Each bar represents the mean of three independent experiments performed in triplicate±SD).

Figure 10A:
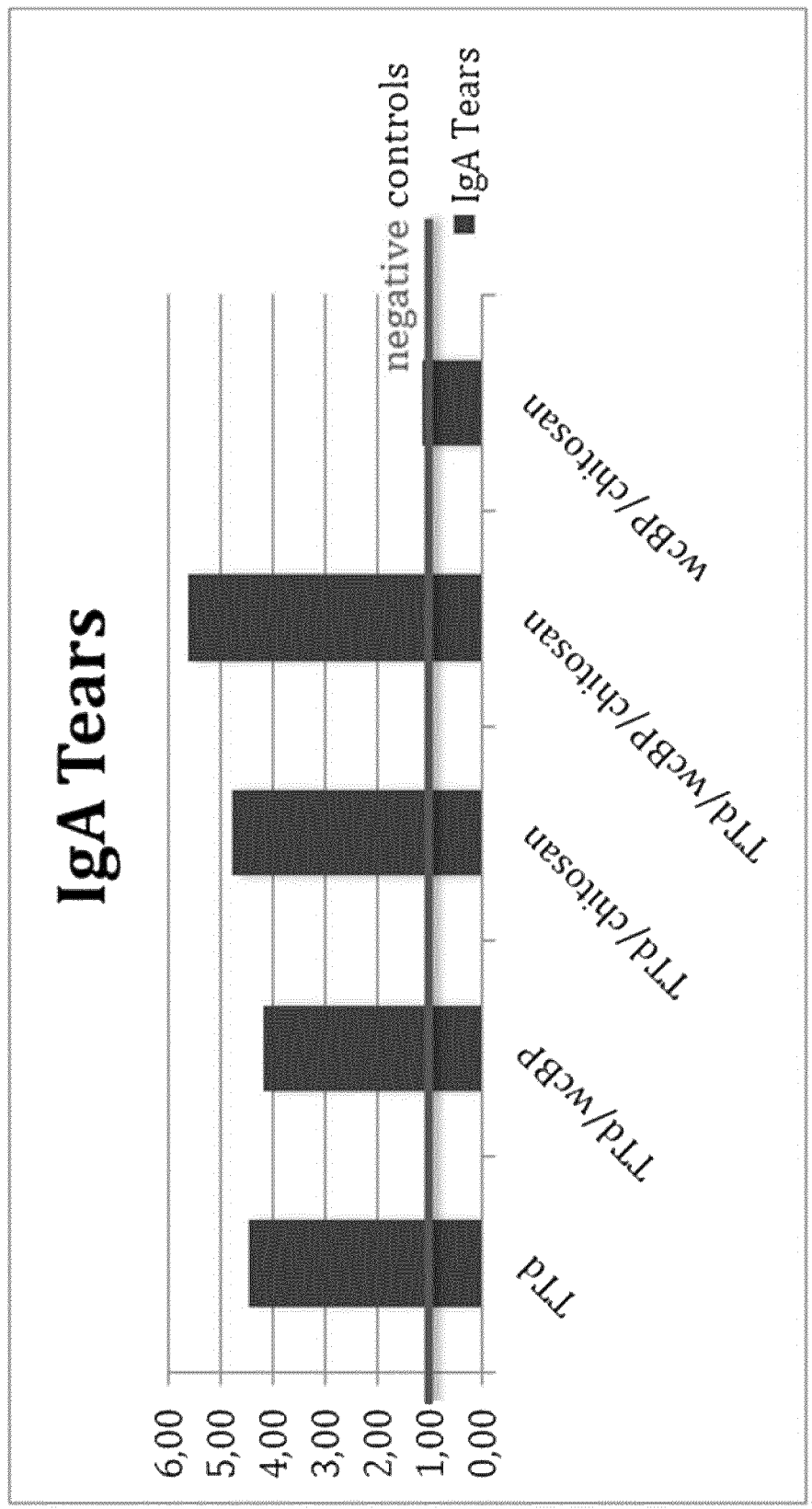
Figure 10B:
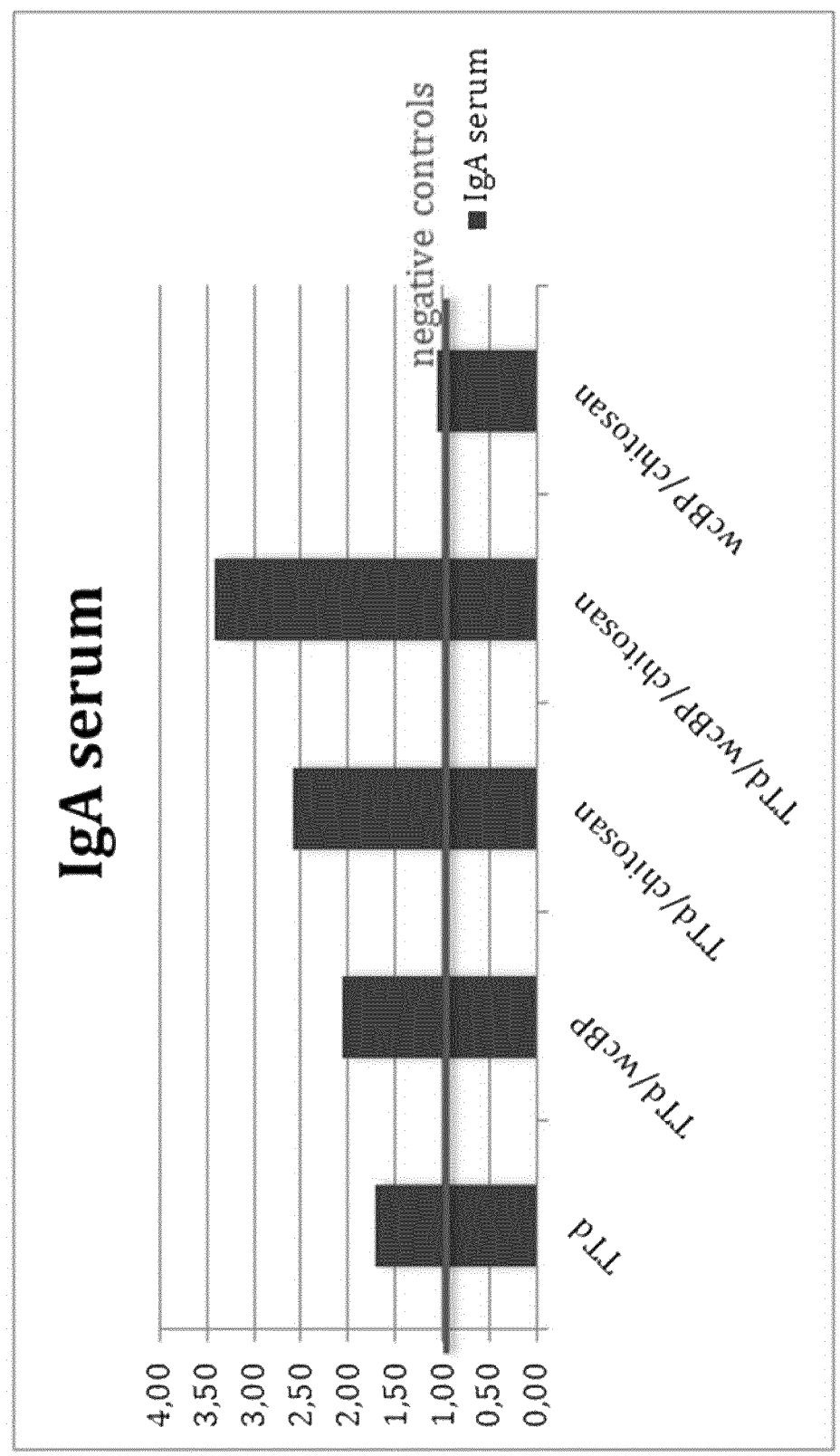

FIG. 10. IgA levels in serum after immunization comparing different groups. Bars represent the factor rise compared to negative control.
 a) IgA in tears
 b) IgA in serum.

BLOOD COLLECTION AND SERA PREPARATION

Samples of blood sera were collected by bleeding from the retro-orbital sinuses a week after the completion of the immunization protocol. The collected sera were complement depleted, aliquoted and stored at −20° C.
Tears Collection
Tear-wash samples were obtained by lavage with 10 µl PBS per eye.
The collected tears were supplemented with a protease inhibitor cocktail (Thermo Scientific, USA) and stored at −80° C.
Detection of TTd-Specific IgA in Mouse Sera and Tears
ELISA plates (MaxiSorp; Nunc, Roskilde, Denmark) were coated (50 µl/well) with TTd (2.5 µg/ml TTd in PBS) by overnight adsorption at 4° C. 1% (w/v) BSA/PBS were applied as a blocking reagent for 2 h at room temperature. This blocking step, as well as all subsequent ELISA steps, were followed by a wash with 0.05% (v/v) Tween 20 in PBS (four times, 200 µl/well). Appropriately diluted non-pooled serum (1:100) and tear (1:2) samples were incubated in the plates for 1 h at room temperature. Ag-specific antibody binding was detected with 1 h incubation at room temperature using biotin-labeled anti-mouse IgA antibody (BioLegend). Antigen-antibody interactions were visualized using the extrAvidin-peroxidase/o-phenylendiamine system (Sigma, Steinheim, Germany). Absorbance was recorded at 492/620 nm (A492/620). The cutoff value for each system were defined according to the A492/620 value obtained from "negative control" wells (1% BSA w/v in PBS as a sample) plus 3×SD. Samples were considered positive when the A492/620 value exceeded the cutoff value.

DETAILED DESCRIPTION OF THE INVENTION

It has been surprisingly found by the inventors that a vaccine formulation is suitable for ocular immunization of a subject which comprises a subunit vaccine antigen in an amount to provoke a protective immune response in a subject, and a corpuscular adjuvant.

Further, it has also been surprisingly found by the inventors that a vaccine formulation is suitable for ocular immunization of a subject which comprises a subunit vaccine antigen in an amount to provoke a protective immune response in a subject, and at least two adjuvants of which at least one is corpuscular.

The antigen may be an isolated antigen, specifically a protein or carbohydrate antigen, a protein subunit antigen or a recombinant protein.

The term "protein subunit antigen" means a single protein molecule with antigenic properties that can assemble or co-assemble with other protein molecules to form a protein complex.

The term "subunit vaccine antigen" or "subunit antigen" according to the present invention refers to an antigen deprived of infectivity, used as a vaccine antigen; such antigens include, but are not limited to isolated proteins, fragments, or carbohydrate antigens, derived from virus, bacteria or any other organism. Such a subunit vaccine antigen may be isolated or extracted from an organism, specifically from a pathogenic organism, such as a naturally occurring bacteria, virus, or any other pathogenic organism.

According to the invention, whole virus or split vaccine is thus not within the scope of the invention.

The term "pathogenic organism" as used herein refers to an organism capable of producing a disease or disorder in a subject. Examples of pathogens include, but are not limited to, viruses, bacteria, protozoa, *rickettsia, chlamydia*, fungi and the like. Pathogens against which vaccines are effective usually include, but are not limited to, viruses, bacteria and the like.

For example, in the case of *Chlamydia*, the subunit antigen specifically is a molecule exposed to the surface of the organism, such as an antigen from the omp2 and/or polymorphic membrane protein family (Pmps).

As an alternative, the subunit vaccine antigen can be a recombinant polypeptide or protein or a fragment thereof or a recombinant carbohydrate which may be prepared by a synthetic or recombinant technology. Such methods are well known and are in common use in the art, and can be performed using commercially available equipment, reagents, vectors and the like.

Specifically, the subunit antigen is originating from a pathogen selected from the group consisting of a subunit antigen derived from bacteria, fungi or virus.

Specifically it can be a subunit antigen derived from *Chlamydia, Clostridia, Brucella, Salmonella* or *Yersinia*. Said antigen may be specifically selected from the group of outer membrane protein 2 (OMP2), class I accessible protein 1 (Cap1), cysteine-rich protein A (CrpA), *Chlamydia* polymorphic membrane proteins (Pmps), specifically PmpA, PmpB, PmpC, PmpD, PmpE, PmpF, PmpG, PmpH, PmpI, *Chlamydia* heat shock protein 60 (HSP60), *Chlamydia* heat shock protein 10 (HSP10), *Chlamydia* protease-like activity factor (CPAF), *Yersinia pseudotuberculosis* (YopD) or a homolog thereof. It may further be an enolase, arginine binding protein (ArtJ), V-type ATP synthase subunit A (AtpA), peptidyl-prolyl cis-trans isomerase (Mip), glycogen synthase (GlgA), iron binding protein (YtgA), Vtype ATP synthase subunit E (AtpE), type III secretion chaperone (SycD), type III secretion proteins SctC or SctJ, tetanus toxoid, herpes simplex virus subunit protein, varicella zoster virus subunit protein or any combinations thereof.

According to an embodiment, the subunit antigen may be a multivalent antigen.

The term "multivalent" according to the specification means antigens that enable multiple, simultaneous interactions with different ligands. It refers to subunit antigens that are able to bind two or more targets and that contain multiple binding sites. Multivalent antigens can be multivalent and multispecific and can therefore bind two or more targets and/or have two or more binding sites for each of the targets. Multivalent antigens like polypeptides, peptides, proteins or carbohydrates can enhance the affinity and specificity of antibody binding.

The term "an amount to provoke a protective immune response in a subject" as used in the present invention means that the subject shows a seroconversion in tears and serum. Absolute values of antibody titers may be different in different species.

Specifically, the subunit antigen is formulated in single dosage form, which comprises the antigen at a dose of at least 1 ng, specifically of at least 2, 3, 4, 5 ng, ranging between 5 ng to 100 μg, specifically between 50 ng and 90 μg specifically between 100 ng and 75 μg, specifically between 500 ng to 50 μg.

The expression "protective immune response" as used herein is intended to mean the ability of a subject to resist, or show delayed onset of symptoms or reduced severity of symptoms or disease, as a result of its exposure to the subunit antigen of a pathogen that otherwise follows contact with the pathogen. According to the invention, protective immunity is achieved by one or more of the following mechanisms: mucosal and cellular immunity. Mucosal immunity is primarily the result of SIgA antibodies on the conjunctival surfaces of the eye. However, due to the lacrimal drainage system, said vaccine may also reach the nasal mucosa as potential site of raising an immunogenic reaction. The SIgA antibodies are generated after a series of events mediated by antigen-processing cells, B and T lymphocytes that result in SIgA production by B lymphocytes on the mucosa-lined tissues of the body. The primary result of protective immunity is the destruction of the pathogen or inhibition of its ability to replicate itself. The expression "humoral immunity" as used herein means the production and presence of IgG and IgA antibodies and IgM antibodies in serum and accessory processes accompanying it including Th2 activation, cytokine production etc.

The term "corpuscular adjuvant" means any adjuvant of a particle or microsphere structure with a particle size of at least 1 nm, specifically of about 10 nm, 50 nm, 100 nm, 200 nm, 300 nm, 400 nm, 500 nm, 600 nm, 700 nm, 800 nm, 900 nm, 1 μm, 10 μm, 15 μm, 20 μm, 25 μm, 30 μm, 35 μm, 40 μm, 45 μm or 50 μm; specifically being in the range from about 1 nm to 50 μm, specifically from about 10 nm to 5 μm.

According to a preferred embodiment of the invention, the average particle size is more than 300 nm.

According to a specific embodiment, the corpuscular adjuvant is a polymer, specifically it is biodegradable. Biodegradable polymeric microspheres can be, but are not limited to particles consisting of polymers of DL-lactide and glycolide (PLG) that biodegrade in vivo into lactic and glycolic acids by hydrolysis. PLG particles are non-immunogenic and have proven safe for human use during parenteral drug delivery.

As a specific embodiment, the biodegradable polymeric microsphere is chitosan or a derivative thereof, for example chitosan-N-acetylcysteine.

The term "microspheres" means small spherical particles, with diameters in the micrometer range, typically 1 μm to 1 mm. Microspheres can also be referred to as microparticles.

According to a specific embodiment, chitosan can be cross-linked to achieve physiologically stable hydrogel. Such chitosan-hydrogel is available under the trade name ViscoGel®. Said cross-linked chitosan may be mixed or covalently linked with the subunit vaccine antigen according to the invention.

According to an alternative embodiment, the corpuscular adjuvant is a non-pathogenic microbial cell preparation, specifically selected from the group consisting of bacteria, more specifically a preparation of bacterial origin, specifically selected from the group consisting of bacteria, specifically inactivated or attenuated bacteria and/or parts or fragments or microspheres or microparticles thereof. The bacteria may be, for example, chemically or heat inactivated according to methods well known by the skilled person.

According to the invention the corpuscular adjuvant may originate from a genus selected from the group consisting of a genus *Bordetella, Lactobacillus, Bifidobacterium* and *Escherichia*, preferably the species *Bordetella pertussis, Lactobacillus* spp., *Bifidobacterum bifidum, Escherichia coli.*

Specifically, whole cell *Bordetella pertussis* is used as adjuvant.

Specifically, the formulation contains more than one corpuscular adjuvant of different types or origins, specifically 2, 3, 4, 5, 6, or more different corpuscular adjuvants. According to a preferred embodiment, one of the adjuvants is chitosan or any derivative thereof.

In a specific embodiment, the inventive formulation comprises the antigen, a polymer and a corpuscular bacterial derivate as adjuvant.

In yet a more specific embodiment, the inventive formulation comprises the antigen, chitosan and whole cell *Bordetella pertussis.*

Specifically, the adjuvant is a molecule, protein or carbohydrate that, when mixed with the subunit antigen, enhances the immune response against said antigen.

The formulation of the present invention may comprise as a further adjuvant a substance selected from glycerol, inulin or plant lectins, preferably, banana lectin (BanLec-1) and type 2 ribosome-inactivating protein (type 2 RIP), mistletoe lectin I (ML-I). CpG, probiotic bacteriocines, a salt of calcium, iron or zinc, an insoluble suspension of acylated tyrosine, acylated sugars, cationically or anionically deriva-tised polysaccharides, or polyphosphazenes.

Specifically, the inventive formulation can further comprise one or more non-corpuscular adjuvants.

Specifically the adjuvant used in the invention is an unspecific adjuvant which does not target antigen specific receptors.

The adjuvant may be selected to be a preferential inducer of a Th1 type of response to aid the cell-mediated branch of the immune response. High levels of Th1-type cytokines tend to favor the induction of cell-mediated immune responses to a given antigen, whilst high levels of Th2-type cytokines tend to favor the induction of humoral immune responses to the antigen. Adjuvant systems which promote a predominant Th1 response include glycerol, CpG as well as suitable corpuscular adjuvant of bacterial origin.

The induction of mixed Th1/Th17 immune responses could be crucial for defense against intracellular parasites, as IFNγ and IL-17 synergistically enhance the resolution of such infections. Furthermore, increases in the production of the pro-inflammatory cytokines IFNγ and IL-17 can be accompanied by concurrently enhanced IL-10 secretion, which is most likely produced to counterbalance the pro-inflammatory responses.

In a specific embodiment, the subunit antigen is conjugated to a carrier. According to an embodiment, the carrier is at least one of a buffer, diluent, encapsulating material or auxiliary agent.

According to the invention, the term "carrier" may originate from the same molecules, proteins or carbohydrates as the adjuvant, however the term "carrier" means that the subunit antigen is linked to the carrier whereas the term "adjuvant" means that the subunit antigen is mixed to the adjuvant but there is no linkage between the two moieties.

A carrier may be a molecule, protein or carbohydrate that is covalently linked to a subunit antigen to increase its immunogenicity when conjugated thereto.

Specifically, conjugation of the subunit antigen to a highly immunogenic carrier protein for enhancing the immunogenicity is provided. Carrier proteins to which subunit antigens can be conjugated are known to the skilled person.

Herein, "protein conjugate" or "carrier conjugate" means a protein comprising one or more subunit antigen molecules that are covalently or non-covalently bound to a carrier protein. Thus, a protein conjugate molecule can comprise a carrier protein and one or more subunit antigen moieties. The carrier protein may be an oligomer. It is also encompassed that the subunit antigens are bound to the carrier protein via linkers.

Methods for conjugating proteins are known to the skilled person.

Examples of carrier proteins are diphtheria toxoid, tetanus toxoid, human serum albumin (HSA), bovine serum albumin (BSA), or hemocyanin such as keyhole limpet hemocyanin (KLH) or subunits thereof.

Specifically, a biodegradable polymeric microsphere, preferably chitosan, a non-pathogenic microbial cell preparation, for example a preparation of bacterial origin, specifically inactivated or attenuated bacteria and/or parts or fragments thereof can be used as carrier according to the invention.

According to a specific embodiment, the inventive formulation comprises an antigen conjugated to chitosan and at least one adjuvant, wherein said adjuvant specifically is corpuscular. The inventive formulation also has the advantage that no ocular inflammation or pathology is induced at the ocular surface after conjunctival vaccination.

The formulation according to the invention may further comprise an antiphlogistic or antibiotic agent, specifically an agent with additional anti-inflammatory properties, specifically histamine antagonists or non-steroidal anti-inflammatory drugs, specifically azithromycin.

The formulation according to the invention can contain the antigen with the corpuscular adjuvant, further containing a carrier and/or an additional adjuvant, wherein the additional adjuvant is a mixture, an adsorbate or a conjugate.

The advantageous formulation according to the invention is used for ocular immunization.

The term "ocular" can be used interchangeably with the term "conjunctival".

The formulation may be administered by ocular or conjunctival application. Conjunctival vaccination can be an effective and efficient route which can easily be administered. Originally prompted by the route of infection, conjunctival administration of the vaccine subunit antigen provides an innovative development.

Most vaccines are licensed for parenteral administration and fail to elicit appropriate mucosal immunity needed for protection against infections with mucosal port of entry (Holmgren and Czerkinsky, Nat. Med, 2005, 11(4), 45-53). Consequently, effective mucosal vaccines are needed as they could contribute to the improvement of global health by stimulating protective immune responses at the site of infection.

Furthermore, the profile of the immune responses induced through the mucosal route confers to several advantages over parenteral vaccination. First, the most effective means of inducing an immune response at a specific effectors' site is localized stimulation, or at least stimulation at a site related in terms of lymph drainage. Second, local exposure to an antigen could result in much higher levels of specific SIgA and an associated mucosal immunologic memory in the region of exposure than in distant sites (Holmgren and Svennerholm, Curr Opin. Immunol., 2012, 24(3), 343-53). Third, in addition to IgA responses, mucosal vaccination induces systemic IgG responses that represent a further defense against invasion by microorganisms or their products. Fourth, in addition to serum IgG and mucosal IgA antibodies, mucosal immunization can stimulate cell mediated responses including helper CD4+ T cells and CD8+ cytotoxic T lymphocytes, the latter being important to combat intracellular pathogens.

It is preferred according to the invention that the protective immune response is a local and systemic one, inducing SIgA and IgG specifically recognizing the subunit antigen.

The invention also provides the use for the inventive formulation in treating a subject by active immunotherapy, wherein the formulation is administered to the subject by the ocular or conjunctival route to provoke an immunomodulation of an immune response in the subject.

The formulation may be administered onto the conjunctival sacs using a device which is applicable for said administration.

The formulation of the invention may also be formulated as depot formulation which provides continuous or prolonged administration.

According to a further embodiment of the invention, the formulation can be used in preventing recurrence of ocular infections in a subject or reduce the severity of sequels.

According to the embodiment, the formulation may be in the form of eye drops or gels, creams, emulsions, spray, aerosol, hydrogel or any other form that is applicable for ocular administration.

For ocular application, solutions containing the vaccine subunit antigen of the invention may be prepared using a physiological saline solution as a major vehicle. The solutions may be maintained at a comfortable pH with an appropriate buffer system. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed. The amount of buffer used may vary. The formulations may also contain conventional, pharmaceutically acceptable preservatives, stabilizers and surfactants.

The vaccine solution applicable according to the invention may include demulcents or film forming materials. Examples of demulcents may include, but are not limited to polymers such as polyvinyl alcohol, povidone, hydroxypropyl methyl cellulose, poloxamers, carboxymethyl cellulose, hydroxyethyl cellulose, acrylates; surfactants such as polyoxyethylene sorbitan monooleate and glycerin. The amount of demulcent may vary.

In some embodiments, the pH of a composition may be from about 7 to about 7.5, or from about 7.2 to about 7.4, or about 7.3.

A solution may also include a preservative. The preservative may vary, and may include any compound or substance suitable for preventing microbial contamination in an ophthalmic liquid subject to multiple uses from the same container. Preservatives that may be used in the formulation disclosed herein include, but are not limited to, cationic preservatives such as quaternary ammonium compounds including benzalkonium chloride, polyquad, and the like; guanidine-based preservatives including polyhexamethylene biguanide (PHMB), chlorhexidine, and the like; chlorobutanol; mercury preservatives such as thimerosal, phenylmercuric acetate and phenylmercuric nitrate; and oxidizing preservatives.

Preferably, the formulations of the present invention are stable in a wide range of temperatures. In one embodiment the vaccine subunit antigens can be reconstituted by mixing pre-measured quantities of each component immediately prior to use.

The invention also provides that the formulation be packaged in a hermetically sealed container such as an ampoule, sachette or single dose units indicating the quantity of formulation.

In one embodiment, the formulation is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the composition is supplied in liquid form in a hermetically sealed container indicating the quantity and concentration of the composition.

In an embodiment of the invention, the formulation is provided as a kit of parts, comprising a component or container containing the antigen; a component containing carrier/adjuvants; and optionally means to dispense the formulation.

Specifically, the invention also provides for a pharmaceutical pack or kit comprising one or more containers filled with one or more of the components of the vaccine formulation of the invention. In a specific embodiment, the kit comprises two containers, one containing the subunit vaccine antigen and the other containing the adjuvant. Said kit of parts may contain also more, preferably 2, 3, 4, 5 or more additional, different adjuvants and with at least one corpuscular adjuvant which may be either mixed in one container or are provided in separate compartments. Associated with such container(s) can be a notice in the form prescribed by a governmental agency regulating the manufacture, use or sale of pharmaceuticals or biological products, which notice reflects approval by the agency of manufacture, use or sale for human administration.

The formulation can be administered in the way that the antigen and the adjuvant are administered either separately or simultaneously.

According to the terms of the invention, the term "subject" can be any singular or plural subject, including, but not limited to humans and animals, e.g. mammals or birds, specifically from horses, poultry, pigs, cattle, rodents and pets. Said subjects can be healthy subjects or any subjects suffering or going to suffer from an ocular disease.

According to the invention, the formulation is formulated as a vaccine for in vivo administration to the subject in such a way that the individual components of the composition are formulated such that the immunogenicity of individual components is not substantially impaired by other individual components of the composition.

The present invention also provides a method for vaccinating or treating a subject by ocular/conjunctival immunization comprising a subunit vaccine antigen in an amount to provoke a protective immune response in a subject, and a corpuscular adjuvant. A method of preventing the recurrence of an ocular infection in a subject is also provided by an embodiment of the invention.

The invention furthermore comprises the following items:

1. A vaccine formulation for ocular immunization of a subject comprising a subunit vaccine antigen in an amount to provoke a protective immune response in a subject, and a corpuscular adjuvant.

2. The formulation according to item 1, wherein the antigen is an isolated antigen, preferably a protein or carbohydrate antigen, a protein subunit antigen or a recombinant protein, 3. The formulation according to item 1 or 2, wherein the antigen is originating from a pathogen selected from the group consisting of bacteria such as *Chlamydia, Clostridia, Brucella, Salmonella, Yersinia* and virus or any combinations thereof.

4. The formulation according to any one of items 1 to 3, comprising at least two adjuvants of which at least one is corpuscular.

5. The formulation according to any one of items 1 to 4, formulated in single dosage form, which comprises the antigen at a dose ranging between 5 ng to 100 μg, preferably between 500 ng to 50 μg.

6. The formulation according to any one of items 1 to 5, wherein the adjuvant is a biodegradable polymer, preferably comprising chitosan.

7. The formulation according to any one of items 1 to 6, wherein adjuvant is a non-pathogenic microbial cell preparation, preferably bacteria, more preferred a preparation of bacterial origin, preferably selected from the group consisting of bacteria, preferably inactivated or attenuated bacteria and/or parts or fragments thereof.

8. The formulation according to any one of items 1 to 7, wherein the adjuvant or carrier originates from a genus selected from the group consisting of a genus *Bordetella, Lactobacillus, Bifidobacterium* and *Escherichia*, preferably the species *Bordetella pertussis, Lactobacillus* spp., *Bifidobacterum bifidum, Escherichia coli.*

9. The formulation according to any one of items 1 to 8, wherein the subunit antigen is conjugated to a carrier and wherein said carrier is preferably a biodegradable polymeric microsphere, preferably chitosan, and/or a non-pathogenic microbial cell preparation, preferably selected from the group consisting of bacteria or a preparation of bacterial origin, preferably inactivated or attenuated bacteria and/or parts or fragments thereof.

10. The formulation according to any one of items 1 to 9, wherein the adjuvant has a particle size ranging from about 1 nm to 50 µm, preferably from about 10 nm to 5 µm, more preferably the particle size is >300 nm.

11. The formulation according to any one of items 1 to 10, which further comprises an antiphlogistic agent, preferably an agent with additional anti-inflammatory properties, preferably azithromycin.

12. The formulation according to any one of items 1 to 11, which comprises the antigen and a carrier or an additional adjuvant, wherein the adjuvant is a mixture, an adsorbate or a conjugate.

13. A formulation for ocular immunization of a subject comprising a subunit vaccine antigen in an amount to provoke a protective immune response in a subject, chitosan and a further corpuscular adjuvant.

14. The formulation according to any one of items 1 to 13, which is provided as a kit of parts, comprising
   a) a component containing the antigen;
   b) a component containing carrier/adjuvants; and optionally
   c) means to dispense the formulation.

15. The formulation according to any one of items 1 to 14, wherein the formulation comprises as a carrier at least one of a buffer, diluent, encapsulating material or formulation auxiliary.

16. The formulation according to any one of items 1 to 15, wherein the subject is selected from the group consisting of humans, horses, birds, poultry, pigs, cattle, rodents and pets.

17. The formulation according to any one of items 1 to 16, which is provided as eye drops, eye spray, eye aerosol or ocular ointment.

18. The formulation according to any one of items 1 to 17 for use in treating a subject by active immunotherapy, wherein the formulation is administered to the subject by the ocular or conjunctival route to provoke a protective immune response in said subject.

19. The formulation according to any one of items 1 to 18 for use in preventing recurrence of ocular infections in a subject.

20. The formulation for use according to items 18 or 19, wherein the antigen and the adjuvant are administered separately or simultaneously.

21. The formulation for use according to any one of items 18 to 20, wherein the protective immune response is a local and systemic one, inducing SIgA and IgG specifically recognizing the antigen.

22. The formulation for use according to item 21 which is formulated as a vaccine for in vivo administration to the subject in such a way that the individual components of the composition are formulated such that the immunogenicity of individual components is not substantially impaired by other individual components of the composition.

23. A method for treating a subject wherein a formulation according to any one of items 1 to 17 is administered to said subject.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Materials and Methods

Mice

Eight-week-old BALB/c and C57BL/6 female mice were used in the experiments. All experiments were approved by the "Ethics Committee for the Welfare of Experimental Animals" and by the committee section at the Institute of Virology, Vaccines and Sera—Torlak and conformed to the Serbian laws and European regulations on animal welfare (Approval No. 011-00-00510/2011-05/2).

Antigens, Adjuvants and Immunization and Bleeding Schedules

BALB/c and C57BL/6 female mice were immunized via the conjunctiva (conj//) with TTd (Institute of Virology, Vaccines and Sera—Torlak, Belgrade, Serbia) as a model antigen (100 µg TTd/PBS per mouse in 10 µl (5 µl per eye) was applied to the conjunctiva), and 2% glycerol (glyc) and merthiolat-inactivated whole cell *B. pertussis* (wBP) (Institute of Virology, Vaccines and Sera—Torlak, Belgrade, Serbia) were used as Th1-promoting adjuvants. These adjuvants were chosen because glyc is commonly used in eye drops for human use at this concentration and because preliminary experiments in which wBP was administered in a corpusculated form or as an adjuvant platform revealed no visible signs of inflammation or infection at the ocular surface. Mice (n=10 per group) were immunized on days 0, 7 and 14 via either the conj// or sc// routes, and the evaluations of local and systemic immune responses were conducted two weeks after the last immunization. According to the applied immunization protocols, the mice were divided into the following four experimental groups: conj//TTd, conj//TTd/glyc, conj//TTd/wBP and sc//TTd. Age-matched, non-immunized mice and conj//glyc- and conj//wBP-treated mice were used as controls.

All vaccines were prepared in situ by mixing defined volumes of the stock TTd and wBPsolutions (both in PBS) or concentrated glycerol (stock solution 85%) in order to prepare vaccines that finally contain:
   10 mg/ml TTd in PBS for conj//TTd
   10 mg/ml TTd and 2% glycerol in PBS for conj//TTd/glyc
   10 mg/ml TTd and $2\times10^8$ cells/ml wBP in PBS for conj//TTd/wBP
   1 mg/ml TTd in PBS for sc//TTd
   2% glycerol in PBS for conj//glyc
   $2\times10^8$ cells/ml wBP in PBS for conj//wBP Obtained solutions were mixed thoroughly by vortexing for 30 minutes and 5 µl per eye (in total 10 µl per mice) was applied via conjunctiva. 100 µl per mice was applied subcutaneously.

Mice that were immunized via the conjunctiva were anaesthetized by intraperitoneal (i.p.) administration of a mixture of xylazine (Sigma-Aldrich, Kansas, Kans., USA) and ketamine (Richter Pharma AG, Wels, Austria). Antigens were applied onto the conjunctival sacs using a micropipette. The mice were maintained under anesthesia for 30 minutes to prevent removal of the immunization solution.

Subcutaneously immunized (sc//) mice were used as a "gold standard" (100 μg TTd/PBS per mouse in 100 μl). The TTd used for the immunizations met the standards for specific and reversed toxicity according to the European Pharmacopoeia requirements.

Sample Collection

Samples of blood sera were collected by bleeding from the retro-orbital sinuses two weeks after the completion of the immunization protocol. The collected sera were complement depleted, aliquoted and stored at −20° C. Tear-wash samples were obtained by lavage with 10 μl PBS per eye. The collected tears were supplemented with a protease inhibitor cocktail (Thermo Scientific, USA) and stored at −80° C.

Detection of TTd-Specific IgG, IgG Subclasses and IgA in Mouse Sera and Tears

ELISA plates (MaxiSorp; Nunc, Roskilde, Denmark) were coated (50 μl/well) with TTd (2.5 μg/ml TTd in PBS) by overnight adsorption at 4° C., and 1% (w/v) BSA/PBS was applied as a blocking reagent for 2 h at room temperature. This blocking step, as well as all subsequent ELISA steps, was followed by a wash with 0.05% (v/v) Tween 20 in PBS (four times, 200 μl/well). Appropriately diluted non-pooled serum (1:100) and tear (1:2) samples were incubated in the plates for 1 h at room temperature. Ag-specific antibody binding was detected with a 1 h incubation at room temperature using biotin-labeled anti-mouse IgG (Sigma, Steinheim, Germany), biotin-labeled anti-mouse IgG1, IgG2a, and IgG2c antibodies (Sigma, Steinheim, Germany) and biotin-labeled anti-mouse IgA antibody (BioLegend). Antigen-antibody interactions were visualized using the extrAvidin-peroxidase/o-phenylendiamine system (Sigma, Steinheim, Germany), and absorbance was recorded at 492/620 nm ($A_{492/620}$). The cutoff value for each system was defined according to the $A_{492/620}$ value obtained from "negative control" wells (1% BSA w/v in PBS as a sample) plus 3×SD. Samples were considered positive when the $A_{492/620}$ value exceeded the cutoff value.

Cells from Draining Lymph Nodes

Submandibular (SMLN) lymph nodes from mice that were immunized via the conjunctiva and from control mice were aseptically isolated, trimmed of all excess tissue and placed in sterile complete RPMI 1640 (Sigma-Aldrich) supplemented with inactivated 5% fetal calf serum (FCS). Lymphocytes were harvested in 5% FCS/RPMI 1640 and passed through sterile steel mesh to remove large particles. Cell suspensions were centrifuged at 1000 rpm (SIGMA 3K18, Sigma Laboratory Centrifuges GmbH) to yield pellets. After centrifugation, the lymphocytes were washed three times in 5% FCS/RPMI 1640 with centrifugation at 1000 rpm (5 min). The cells were finally diluted in 10% FCS/50 μM β-mercaptoethanol/RPMI 1640 to a concentration of $2 \times 10^6$ cells/ml. The viability of these cell preparations, as determined by trypan blue exclusion, was greater than 95%. Lymphocytes ($2 \times 10^6$ cells/ml) were used for ELISA or were stimulated in vitro (37° C., 5% $CO_2$, 48 h). As a stimulus, TTd was added to the cultures at 5 μg/ml.

Abundance of TTd-Specific B Cells within the Total mIgG+ B Cell Population in Draining Lymph Nodes The abundance of the specific B cell population was investigated using an ELISA-based procedure. SMLN suspensions were simultaneously assessed for both the amount of total mIgG+ cells as well as TTd-specific mIgG+ B cells. All washes were conducted in PBS. For the detection of total mIgG+ B cells, MaxiSorp microtiter plates (Nunc) were coated (50 μl/well, overnight at 4° C.) with commercially available polyclonal anti-mouse IgG (10 μg/ml PBS; Sigma M 0659). Suspensions containing $2 \times 10^5$ cells/ml were added to the blocked (1% BSA in PBS) anti-mouse IgG-coated wells (50 μl/well) to assess the total number of mIgG+ B cells. The coating procedure that was previously described in the Materials and Methods section (for the detection of IgG and IgA specific for TTd in the sera and tears) was applied for the detection of TTd-specific B cells. For this assessment, suspensions containing $2 \times 10^6$ cells/ml were used (50 μl/well). TTd-specific and total mIgG+ B cells were detected using polyclonal alkaline phosphatase-labeled anti-mouse IgG (Sigma, A-3562). Non-specific binding was assessed in wells that were blocked but were not coated with reagents (i.e., those lacking capture antibody and specific antigen). The amount of bound alkaline phosphatase-labeled antibodies per well was evaluated using p-nitrophenyl phosphate as a substrate. The transformation of p-nitrophenyl phosphate by alkaline phosphate occurred at the same rate in all wells. The abundance of specific B cells within the mIgG+ population was calculated for each individual animal. Using the $A_{405}$ value measured upon the evaluation of total mIgG-expressing cells ($A_{405tot}$) and the corresponding $A_{405}$ value measured upon specific B cell assessment ($A_{405spec}$), the relative abundance (RA) of specific B cells was calculated as follows: RA=($A_{405spec}$×100)/$A_{405tot}$.

MTT Assay

Following 48 h of incubation (5% $CO_2$, 37° C.), the plates containing the cell cultures were centrifuged (800 rpm, 10 min), and the supernatants were decanted. DMEM/25 mM HEPES/0.2% $NaHCO_3$ containing 500 μg/ml of 3-(4,5-dimethylthiazol-2-yl)-2,5-diphenyltetrazolium bromide (MTT) (Sigma-Aldrich) was added to the experimental wells (100 μl/well), and the cells were incubated (37° C., 5% $CO_2$, 4 h). Reactions were halted by the addition of 10% SDS/10 mM HCl (100 μl/well). After an overnight incubation at 37° C., absorbance values were measured at 580 nm ($A_{580}$) using a spectrophotometer (Ascent 6-384 [Suomi], MTX Lab Systems Inc., Vienna, Va., USA). The number of viable cells per well (NVC) was calculated from a standard curve drawn as the number of cells plotted against $A_{580}$. Standard curves were drawn for both mouse strains (BALB/c and C57BL/6). Discrete pools of non-stimulated cells were taken from each strain and, after counting the cells using a hemocytometer, were then used as standards. Standard suspensions were plated in serial dilutions prior to centrifugation and were then treated identically to the experimental wells that received stimulated aliquots. A proliferation index (PI) for each stimulated cell suspension was calculated per individual source animal. The PI index was defined as the ratio of NVC present in stimulated (S) samples to NVC present in non-stimulated (nS) samples, such that PI=NVCS:NVCnS.

Cytokine Profile of Draining Lymph Node Cells

The production of IFNγ, IL-4, IL-17A and IL-10 was analyzed by measuring the supernatant concentrations of non-stimulated and TTd-stimulated SMLN lymph node cultures using sandwich ELISAs with commercially available monoclonal antibodies (eBioscience). Unlabeled monoclonal Abs specific for IFNγ (1 μg/ml), IL-4 (2 μg/ml), IL-17A (1 μg/ml) or IL-10 (1 μg/ml) were coated onto microtiter plates (MaxiSorp, Nunc) by overnight adsorption at 4° C., and 1% BSA/PBS (w/v) was used to block the plates (2 h) at room temperature. Blocking and all subsequent ELISA steps were followed by a wash step with 0.05% (v/v) Tween 20 in PBS (four times, 200 μl/well). Lymph node supernatants were incubated in the plates (1 h) at room temperature. Biotin-labeled Abs specific for IFNγ (2 μg/ml), IL-4 (1 μg/ml), IL-17A (1 μg/ml) or IL-10 (1 μg/ml) and formulated in 1% BSA/PBS (w/v) were then added to the wells and incubated for 1 h at room temperature. The extrAvidin-alkaline phosphatase/p-nitrophenyl phosphate system (Sigma-Aldrich) was used to visualize antigen-Ab interactions. Absorbance was monitored at 405 nm ($A_{405}$). The cutoff value for each system was calculated as the displayed $A_{405}$ reading measured in the negative control well (1% BSA/PBS used as a sample) plus 3×SD. Standard curves were created using commercially available recombinant mouse IFNγ, IL-4, IL-17A and IL-10.

Protection Assay Against Tetanus Toxin (TTn)

Four weeks after the course of conj// and sc// immunizations, anesthetized mice (n=6) were challenged with a lethal dose (2×$LD_{50}$) of TTn by intraperitoneal (i.p.) injection. The animals were monitored for weight loss and survival every day for 5 days.

Tolerability at the Ocular Surface

Signs of ocular irritation were monitored in BALB/c and C57BL/6 mice immunized via the conjunctiva and in non-immunized controls daily during the course of immunization and every week for the remainder of the study by two unbiased observers. Conjunctival hyperemia, edema and corneal clarity were assessed using magnifying loupes.

Statistical Analysis

The results are presented as the mean value±standard error (SE). The statistical significance of the observed differences was evaluated using the t-test for independent groups. A probability (P) value of 0.05 was set as the limit of significance (software: ORIGIN 8.0). The correlation between variables was evaluated by Pearson's bivariate correlation analysis (software: IBM SPSS Statistics 20).

Results

SIgA Levels in Tears Increased in Both Mouse Strains Following TTd Immunization Via the Conjunctiva Versus Subcutaneous Immunization Immunization through the conjunctival route resulted in levels of TTd-specific SIgA in both mouse strains that were significantly higher than those found in the tears of syngeneic control mice (non-immunized and adjuvant-alone immunized) as well as mice that were subcutaneously immunized with TTd (FIG. 1). The amount of TTd-specific SIgA detected in the tears of sc//TTd-immunized mice was negligible and was similar to the levels found in tears from non-immunized mice. Although the mean levels of SIgA in the tears of conj//TTd/wBP-immunized mice were higher compared to levels in conj//TTd- and conj//TTd/glyc-immunized mice of the same strain, these differences were not significant. With regard to the different mouse strains, BALB/c mice exhibited greater SIgA concentrations in tears than C57BL/6 mice, although this difference was not significant.

Serum IgG and IgA Levels Increased Following Conjunctival Immunization with TTd when wBP was Used as an Adjuvant In both mouse strains, conjunctival immunization with TTd, TTd/glyc or TTd/wBP resulted in significantly higher levels of TTd-specific IgG (FIG. 2a) and IgA (FIG. 2b) in the serum compared to serum from non-immunized or adjuvant-alone-immunized mice.

Generally, anti-TTd IgG and IgA levels in the serum of conjunctively immunized BALB/c mice were higher than the levels in the serum of C57BL/6 mice treated the same way. A comparison of the syngeneic mice immunized with TTd via the conjunctiva revealed that, except in the case of anti-TTdIgG in BALB/c mice, there were no significant differences in the levels of sera anti-TTd antibodies among the mice. The conjunctival administration of TTd mixed with wBP promoted a significantly higher (P<0.05) systemic production of TTd-specific IgG than the administration of TTd alone (P<0.05). In comparison to the "gold standard" (sc// immunization with TTd without adjuvant), the levels of serum TTd-specific IgG were significantly lower in all mice that were immunized with TTd via the conjunctiva (P<0.0005 in comparison to sc//TTd-immunized mice of the same strain). Regarding the level of sera TTd-specific IgA, the conjunctival administration of TTd in BALB/c mice was superior to subcutaneous administration (P<0.05), whereas in C57BL/6 mice an opposite situation is recorded (P<0.05).

Serum IgG Antibody Subclass Responses Provided the Initial Evidence that Immunization with TTd Via the Conjunctiva can Induce Skewing of TTd-Specific Immune Responses Towards a Th1-Type Response When the TTd-specific serum IgG subclass immune responses were assessed, the ratios of IgG1 and IgG2a in BALB/c mice and IgG1 and IgG2c in C57BL/6 mice were significantly higher in sc//-immunized mice in comparison to each group of mice that were immunized via the conjunctiva (P<0.05 for BALB/c and P<0.0005 for C57BL/6). The rise in the abundance of IgG antibodies that are dependent on IFNγ for secretion (i.e., IgG2a in BALB/c and IgG2c in C57BL/6) in the TTd-specific sera IgG pool of conjunctively immunized mice indicated that Th1 immune response skewing had occurred. Although there were differences in the IgG1/IgG2a,c ratios among syngeneic conjunctively immunized mice, these differences were not significant.

An Increased Population of TTd-Specific B Cells within the Total SMLN B Cell Population Strongly Correlated with Levels of Sera TTd-Specific Antibodies An increased population of TTd-specific B cells was found within the total mIgG+ B cell population in the draining lymph nodes of mice immunized with TTd via the conjunctiva (FIG. 3). Compared to the syngeneic age-matched control group, as well as groups treated with glycerol or wBP alone, a significantly higher frequency of mIgG$^+$ TTd-specific B cells within the draining SMLN was evident in all these groups (P<0.05). The greatest abundance of TTd-specific B cells in mice immunized via the conjunctiva was found in the TTd/wBP groups (P<0.005 in comparison to the corresponding n.c.). Bivariate correlation analyses confirmed a strong correlation between the levels of TTd-specific IgG in the serum and the relative abundance of TTd-specific B cells in the draining lymph nodes (P<0.01; for BALB/c and C57BL/6 mice, the Pearson correlation coefficients were 0.787 and 0.832, respectively).

The Greatest Proliferation of Draining SMLN Cells in Response to TTd was Observed Using wBP as an Adjuvant SMLN cells from immunized mice were used to perform a cell proliferation assay (FIG. 4). Following immunization via the conjunctiva, both mouse strains showed almost identical trends in proliferation index values following stimulation with TTd. Among the groups that were immunized via the conjunctiva, SMLN cells from the TTd/wBP group showed the highest proliferation index values in response to TTd. In C57BL/6 mice, PIs recorded for the conj//TTd/wBP group were significantly higher than those for the conj//TTd group.

Immunization with TTd/wBP Via CALT Promoted the Establishment of a Th1 TTd-Specific Immune Response SMLN cells from immunized and non-immunized control BALB/c and C57BL/6 mice were stimulated in vitro with TTd and analyzed for the production of IFNγ (a marker of Th1 responses), IL-4 (a marker of Th2 responses), IL-17A (a marker of Th17 responses) and IL-10 (a cytokine with regulatory and anti-inflammatory roles) (FIG. 5). As shown in FIG. 5, SMLN cells produced the tested cytokines without any additional stimulation during in vitro cultivation. Some treatment-dependent differences in the production of specific cytokines were marked, although the majority of the differences were not significant (data not shown). However, in vitro TTd stimulation generally altered the production of the tested cytokines in the SMLN cultures derived from conjunctively immunized mice.

A conjunctival multi-dose application of TTd alone, without an adjuvant, in BALB/c mice resulted in the diminished capacity of draining SMLN cells to produce IFNγ (P<0.05 in comparison to the BALB/c n.c. group) and IL-4 (the concentration was below the limit of detection) but an enhanced capacity to produce IL-17A (P<0.05 in comparison to the BALB/c n.c. group) following in vitro TTd stimulation. In C57BL/6 mice treated in an identical manner, TTd stimulation of SMLN cells induced IL-10 secretion (P<0.005 in comparison with the C57BL/6 n.c. group), whereas the production of IFNγ, IL-17A and IL-4 was not affected in comparison to non-immunized mice.

Conj//TTd/glyc immunization caused a reduction in the capacity of SMLN cells from BALB/c mice to secrete IFNγ and IL-4 (P<0.005 in comparison to the n.c. group) upon TTd stimulation. In these cultures, only the secretion of IL-17A was augmented (P<0.005 in comparison to the n.c. group). In contrast, SMLN cells from conj//TTd/glyc-immunized C57BL/6 mice produced IFNγ (P<0.05) and IL-4 (P<0.005) in higher quantities upon in vitro TTd stimulation than did the SMLN cells from control mice, whereas the production of IL-17A was similar to that detected in SMLN cultures from non-treated mice.

Significantly higher levels of both IFNγ (P<0.005 for BALB/c, P<0.05 for C57BL/6) and IL-17A (P<0.005 for both strains) upon in vitro TTd stimulation were detected in SMLN cell cultures obtained from conj//TTd/wBP-treated mice compared to the corresponding TTd-stimulated control cell cultures obtained from non-immunized mice. The increased production of IFNγ upon TTd stimulation was also observed in cultures from conj//wBP-immunized mice (for both mouse strains, P<0.05 in comparison to the corresponding n.c. group), whereas the production of IL-17A was not significantly greater than that observed in corresponding non-stimulated cultures. In TTd-stimulated cultures of SMLN cells from conj//TTd/wBP BALB/c mice, IL-10 production was also stimulated (P<0.05) in addition to in IFNγ and IL-17A production, whereas IL-4 production was diminished (P<0.005) in comparison to a reference culture of non-treated murine lymph node cells. In C57BL/6 mice, TTd stimulation did not affect the secretion of IL-4 by cells from conj//TTd/wBP lymph nodes but augmented the production of IL-10 (P<0.005 in comparison to the n.c. group).

TABLE 1

Intensity of humoral and cellular immunity responses comparing conjunctival and subcutaneous route of administration of PmpC +/− adjuvant.

|  | conj//PmpC alone | conj//PmpC with adjuvant | sc//PmpC alone | s//PmpC with adjuvant |
| --- | --- | --- | --- | --- |
| Anti-PmpC IgA in tears | ++ | +++ | + | + |
| Anti-PmpC IgG in tears | + | + | ++ | ++ |
| Anti-PmpC IgA in serum | + | ++ | + | + |
| Anti-PmpC IgG in serum | + | + | +++ | +++ |
| IFN-gamma - in vitro proliferation, lymphocytes from draining lymph nodes stimulated with PmpC | ++ | +++ | + | + |

Conjunctival Immunization with TTd Mixed with wBP Partially Protects BALB/c and C57BL/6 Mice Against Lethal Challenge with TTn Treatment-dependent survival upon challenge with a lethal dose of TTn was similar in both mouse strains. All subcutaneously immunized mice survived challenge with a lethal dose of TTn. All non-immunized mice, as well as mice conjunctively immunized with TTd alone, TTd/glyc, glycerol or wBP, died on the first day post-challenge. Among the conjunctively immunized mice of both strains, only 33.3% of mice immunized with TTd/wBP survived the TTn challenge. It is evident that the survival rate of conj//TTd/wBP-immunized mice was lower than that of subcutaneously immunized mice (P=0.0001) but was significantly greater than that of the non-treated age-matched control group and other groups treated via the conjunctiva (P=0.028). The survival of sc//TTd- and conj//TTd/wBP-immunized mice, as well as age-matched control mice, upon challenge with a lethal dose of TTn is depicted in FIG. 6. Bivariate correlation analyses showed that the survival rates of both mouse strains upon challenge with TTn positively correlate to the level of sera anti-TTd IgG (P<0.01; for BALB/c and C57BL/6 mice, Pearson correlation coefficients were 0.817 and 0.511, respectively).

No Ocular Irritation or Pathology was Observed at the Ocular Surface of Conjunctively Immunized Mice Non-biased observers did not detect any signs of inflammation at the ocular surfaces of either mouse strain following immunization via the conjunctiva, as the eyes of non-immunized and sc//-immunized mice were visually identical to those of mice immunized via the conjunctiva. In addition, all mice remained healthy until the time of sacrifice, as there were no observed behavioral changes or weight loss during the course of immunization.

Example 2

Materials and Methods

Cell Culture

HCjE cells, kindly provided by Prof. Ilene Gipson (Schepens Eye Research Institute, HarvardMedical School, Boston), were maintained in keratinocyte serum-free medium (LifeTechnologies, Paisley, UK) at 37° C./5% $CO_2$ and 95% humidity. The medium was changed every second day, and the cells were passaged at 70% confluence. Cells were harvested by trypsinisation (0.05% Trypsin/0.02% EDTA in PBS, PAA Laboratories GmbH, Pasching, Austria) and seeded at a density of 30.000 cells/well in 6-well plates (Greiner Bio-One, Kremsmünster, Austria) for subsequent flow cytometric analysis and in 24-well imaging plates (PAA Laboratories GmbH, Pasching, Austria) for laser scanning microscopy.

Corpuscular Adjuvants of Bacterial Origin Labelled with Atto488 Dye

Lyophilised corpuscular adjuvants of bacterial origin were reconstituted in 0.1 M sodium bicarbonate buffer (pH 8.5, PAA Laboratories GmbH, Pasching, Austria) and incubated with Atto488 dye (2 mg/ml in DMSO; ATTO-TEC GmbH, Siegen, Germany) for 1 hour while stirring at 2000 rpm. Atto488-labelled corpuscular adjuvants of bacterial origin were washed 5 times with PBS to remove unbound dye and diluted in keratinocyte serum-free medium (Life Technologies, Paisley, UK).

Live Cell Staining for Laser Scanning Microscopy

Atto488-labelled corpuscular adjuvants of bacterial origin [100, 1000, and 10.000 corpuscular adjuvants of bacterial origin per HCjE cell] were applied to confluent cultures of HCjE cells, and plates were centrifuged at 1200 rpm for 15 min to accelerate the attachment. After this initial step, cells were incubated at 37° C./5% $CO_2$ for another 15 min and 105 min, respectively (incubation time in total was 30 and 120 minutes). HCjE cells were washed six times with PBS, and cells on imaging plates, stained with CellMask plasma membrane stain (5 μg/ml; Molecular Probes Inc., Eugene, Oreg., USA) for 5 min at 37° C., were directly subjected to live cell staining. 4',6-diamidino-2-phenylindole (1 μg/ml; Sigma Aldrich, St. Louise, Mo., USA) was used as a counterstain. To assess only the signal of internalised corpuscular adjuvants of bacterial origin, the fluorescent signal of corpuscular adjuvants of bacterial origin attached to cell surfaces was quenched by incubation with 0.4% trypan blue solution (Sigma Aldrich, St. Louise, Mo., USA) in PBS for 5 min. Plates were mounted and examined by laser scanning microscopy (Zeiss Axiovert 100, Carl Zeiss, Vienna, Austria).

Flow Cytometry Analysis of the Atto488-Labelled Corpuscular Adjuvants of Bacterial Origin Internalization by HCjE Cells The uptake of corpuscular adjuvants of bacterial origin by HCjE cells was analysed by flow cytometry. The cells were prepared the same way as it was described in the section "Live cell staining for laser scanning microscopy". Cells were than incubated at 37° C./5% $CO_2$ for another 15 min and 105 min, respectively (control cells were incubated either with non-labelled corpuscular adjuvants of bacterial origin at 37° C./5% $CO_2$ or with Atto488-labelled corpuscular adjuvants of bacterial origin on ice). HCjE cells were washed six times with PBS to remove the excess of corpuscular adjuvants of bacterial origin. HCjE cells were detached by trypsinisation (0.05% Trypsin/0.02% EDTA, PAA Laboratories GmbH, Pasching Austria), washed three times with 2% BSA/PBS (Sigma Aldrich, St. Louise, Mo., USA), and resuspended in 0.5 ml of this solution. Cells were analysed on a BD FACScan™ (BD Biosciences, San Jose, Calif., USA).

Dead cells were excluded according to their forward and side scatter properties. Data were analysed using FlowJo Software version 9.3.2 (Tree Star Inc., Ashland, Oreg., USA).

Cytotoxicity Assay

For the assessment of possible cytotoxic effects of corpuscular adjuvants of bacterial origin on HCjE cells, cells were seeded at a density of 4×104 cells in 96-well plates. corpuscular adjuvants of bacterial origin were applied at 100, 1000 and 10.000 corpuscular adjuvants of bacterial origin/cell, and plates were centrifuged at 1200 rpm for 15 minutes. Cells were incubated under standard conditions for 15 min and 105 min to reach total co-incubation times of 30 min and 120 min. After co-incubation, these cells were washed extensively with PBS. Supernatants were collected and stored at −80° C. until the measurements. An additional number of cells, after washing with PBS, were incubated for another 24 hours for detection of possible delayed cell death. Cytotoxicity was evaluated by measurement of lactate dehydrogenase (LDH) that was released to the culture medium upon damage of the plasma membrane with a commercially available WST-based assay (LDH Cytotoxicity Assay Kit II, BioVision, Milpitas, Calif., USA) according to the manufacturer's instructions.

Inoculation of Corpuscular Adjuvants of Bacterial Origin into Guinea Pig Eyes

To detect the uptake of corpuscular adjuvants of bacterial origin in vivo, the corpuscular adjuvants of bacterial origin were applied into the conjunctival sac of guinea pigs eyes. All experiments were conducted in agreement with the International and National Guidelines for the Care and Use of Laboratory Animals and were accepted by the Animal Care Committee at the Institute of Microbiology, Sofia. Female Hartley strain guinea pigs (300 to 350 g) were obtained from Charles River Laboratories and were housed separately in cages covered with fiberglass filter tops. Six guinea pigs were anaesthetised with a mixture of ketamine (30 mg/kg) and xylazine (2 mg/kg) administered intramuscularly, and 25 μl of PBS containing 1×107 corpuscular adjuvants of bacterial origin particles were instilled directly into the conjunctival sacs of both eyes. Six guinea pigs were used as sham controls and received only PBS. After 120 min the animals were euthanised by intramuscular administration of an overdose mixture of xylazine and ketamine. Conjunctival tissue was removed and fixed in 1% formaldehyde in PHEM buffer, and paraffin-embedded sections were processed for immunohistochemistry. Additionally, the sections were routinely stained with haematoxylin and eosin (H&E) for a pathology evaluation.

Eye Pathology Examination

In accordance with OECD 405 guidelines for the testing of chemicals (in vivo test for acute eye irritation/corrosion), 2 hours post-inoculation the animal discomfort and clinical signs in the conjunctiva, corneas, and lids were macroscopically evaluated by a trained clinician for possible acute toxicity of the corpuscular adjuvants of bacterial origin. Additionally, conjunctival sections (4 μm) were evaluated in a masked fashion to determine eventual modification of the corneal, limbal, or conjunctival epithelia; edema in lid tissues; presence of inflammatory neutrophils, eosinophils, mast cells or lymphocytes; and any other abnormalities.

Immunohistochemistry Assay

To localize the corpuscular adjuvants of bacterial origin in the guinea pig conjunctival tissue and confirm the uptake in vivo, immunohistochemistry studies were performed. Paraffin sections of guinea pig conjunctival tissue taken 120 minutes after inoculation with corpuscular adjuvants of bacterial origin were deparaffinized and brought to water. After brief wash in PBS with 0.025% Triton-X 100, sections were blocked with 10% BSA for 2 hours at room temperature and incubated with cell-adsorbed polyclonal rabbit anti-corpuscular adjuvants of bacterial origin antisera (Institute of Virology, Vaccines and Sera—Torlak, Belgrade, Serbia), 1:500 dilution in 1% BSA in PBS overnight at 4° C. Control sections were incubated with antibody diluent alone. After 1% BSA-PBS washing, sections were incubated with fluorophore-labelled secondary antibody (CF488A goat anti-Rabbit, Sigma), 1:250 dilution in 1% BSA, for 1 hour at room temperature. After rinsing in PBS and brief wash in distilled water, sections were in DAKO fluorescent mounting medium (DAKO Corp. Carpinteria, Calif., USA). Sections were examined by fluorescence microscopy (Zeiss Axio Observer Z1, Carl Zeiss, Vienna, Austria).
Results
HCjE Cells Efficiently Internalize Corpuscular Adjuvants of Bacterial Origin Laser scanning microscopy of HCjE cells co-incubated with corpuscular adjuvants of bacterial origin confirmed the internalisation of corpuscular adjuvants of bacterial origin. The presence of internalized corpuscular adjuvants of bacterial origin within the cytoplasm was proved by quenching of the fluorescent signal coming from corpuscular adjuvants of bacterial origin eventually attached to HCjE cells surface by using trypan blue solution. Samples that did not undergo the quenching procedure showed distinctively more corpuscular adjuvants of bacterial origin attached and/or internalised than samples that underwent quenching (data not shown). Quantification of the uptake efficiencies showed that corpuscular adjuvants of bacterial origin are internalised into HCjE cells in a time- and dose-dependent manner. Uptake of corpuscular adjuvants of bacterial origin by HCjE cells was detected 30 minutes after administration of Atto488-labelled corpuscular adjuvants of bacterial origin into cell culture. Prolonged, 120 minutes, incubation of HCjE with corpuscular adjuvants of bacterial origin led to significantly increased number of cells efficiently internalizing corpuscular adjuvants of bacterial origin.

Figure 9:
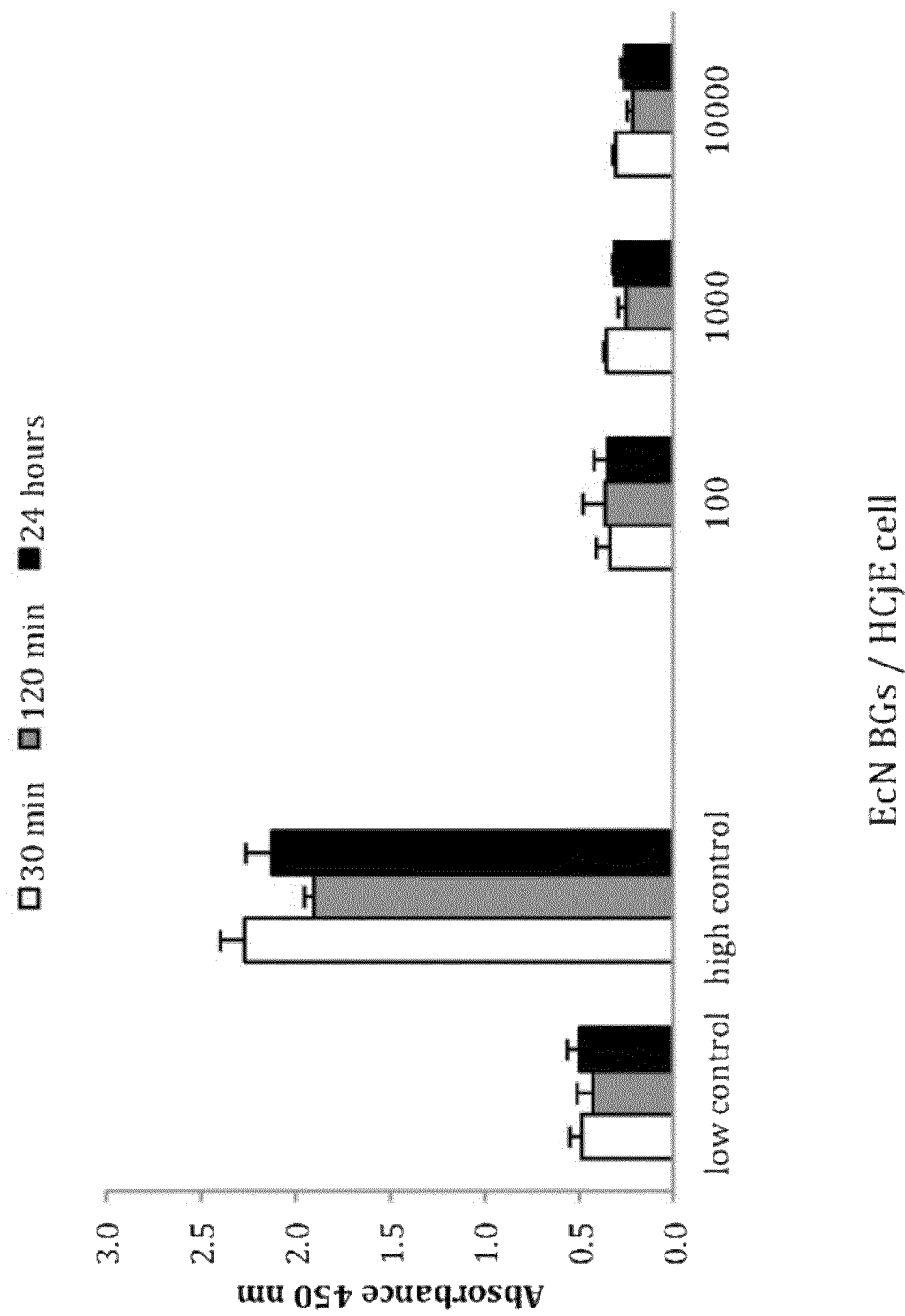

Irrespective to the corpuscular adjuvants of bacterial origin amount, their internalization by HCjE cells after 120 minutes co-incubation was significantly higher than the internalization observed after 30 minutes. The fact that percentages of HCjE cells that internalised corpuscular adjuvants of bacterial origin in cultures incubated for 30 minutes with 10.000 corpuscular adjuvants of bacterial origin/HCjE cell and 120 minutes with 1000 corpuscular adjuvants of bacterial origin/HCjE cell were similar (P=0.301) implies that, in the respect of percentage of HCjE cells that internalised corpuscular adjuvants of bacterial origin, the lower amount of corpuscular adjuvants of bacterial origin could be compensated by prolongation of incubation time and vice versa. FACS analysis revealed similar results to those from the microscopic evaluation.
Corpuscular Adjuvants of Bacterial Origin have No Cytotoxic Effect on HCjE Cells The measurement of LDH release as a reaction to cytotoxic effects decreasing cell viability was performed to elucidate the effect of corpuscular adjuvants of bacterial origin in contact with HCjE cells. Co-incubation of HCjE cells with corpuscular adjuvants of bacterial origin did not result in any adverse effects on cellular metabolic activities. The LDH release levels were less than in the low control, indicating that there were no cytotoxic effects neither after treatment with corpuscular adjuvants of bacterial origin for 30 and 120 min, respectively, nor after 24 hours of incubation at 37° C./5% $CO_2$ after washing off corpuscular adjuvants of bacterial origin from the cells (FIG. 9).
Corpuscular Adjuvants of Bacterial Origin does not Cause Ocular Pathology in Guinea Pig Seven days before the experiments began, the animals presented no clinical signs of diseases, and ocular surface structures were normal. Pathological analysis of the guinea pig eyelids confirmed the presence of normal ocular surface structures in both treated eyes and control. Some of the guinea pigs (n=4) were monitored additionally for 7 days and no signs of any ocular pathology were noticed at any time point (data not shown).

Conjunctival, limbal, and corneal epithelia displayed normal numbers of cell layers composed of cells with appropriate morphologies in both treated eyes and corpuscular adjuvants of bacterial origin control without the presence of inflammatory cells of any type.
Corpuscular Adjuvants of Bacterial Origin are Localized to Conjunctival Epithelial Cells in Guinea Pig Positive staining for corpuscular adjuvants of bacterial origin was detected in all samples to which corpuscular adjuvants of bacterial origin were added, and in none of the samples originated from non-treated guinea pigs. We detected corpuscular adjuvants of bacterial origin within guinea pig conjunctival epithelial cells 120 min after inoculation of corpuscular adjuvants of bacterial origin into outbred guinea pigs. Analysis of lymph nodes, spleen, eye and brain sections from these guinea pigs showed no evidence of corpuscular adjuvants of bacterial origin (data not shown).

Example 3

Experiments Concerning the Uptake of Corpuscular Adjuvants of Bacterial Origin by HCjE Cells The influence of chitosan on the uptake of corpuscular adjuvants of bacterial origin by HCjE cells is tested.
Methods:

HCjE cells were seeded onto chamber slides at a density of $2\times10^8$ cells/well and incubated at 37° C. overnight. $2\times10^8$ of corpuscular adjuvants of bacterial origin labelled with ATTO-390 (Sigma-Aldrich, St. Louis, Mo.) dissolved in boric acid buffer (BAB), 0.05% chitosan-fluorescein isothiocyanate (FITC; Akina, USA) dissolved in BAB, and $2\times10^8$ of labelled corpuscular adjuvants of bacterial origin dissolved in 0.05% labelled chitosan were added to separate wells containing HCjE cells for 30 minutes. The cells were washed with PBS, quenched with 0.4% trypan blue for 5 minutes and stained with CellMask plasma membrane stain (2.5 μg/ml; Molecular Probes, Inc., Eugene, Oreg.) for 5 minutes, both at 37° C. Then the cells were fixed with 4% PFA, mounted and examined by epifluorescence microscopy (Zeiss Axiovert 100; Carl Zeiss GmbH, Vienna, Austria). Results are shown in FIG. 7.
Results:

As demonstrated in previous experiments, corpuscular adjuvants of bacterial origin are readily taken up by the HCjE cells. The addition of chitosan significantly increased the uptake of corpuscular adjuvants of bacterial origin into the HCjE cells. (FIG. 8)
Conclusions:

The uptake of corpuscular adjuvants of bacterial origin by HCjE cells was improved by the addition of chitosan.

Example 4

The Combination of Antigen and Corpusculate Bodies (*Bordetella Pertussis*) and Adjuvants (Chitosan 0.1%) Increases Tear and Sera IgA Levels Further experiments were performed to analyze if the combination of antigen & corpusculate adjuvants (*Bordetella pertussis*, chitosan 0.1%) could increase tear and sera IgA levels necessary to fight mucosal infections. The combination of the 3 components showed the highest rise in IgA antibody titers in tears and sera when compared to the other immunization groups.

Methods:

Blood Collection and Sera Preparation

Samples of blood sera were collected by bleeding from the retro-orbital sinuses a week after the completion of the immunization protocol. The collected sera were complement depleted, aliquoted and stored at −20° C.

Tears Collection

Tear-wash samples were obtained by lavage with 10 µl PBS per eye.

The collected tears were supplemented with a protease inhibitor cocktail (Thermo Scientific, USA) and stored at −80° C.

Detection of TTd-Specific IgA in Mouse Sera and Tears

ELISA plates (MaxiSorp; Nunc, Roskilde, Denmark) were coated (50 µl/well) with TTd (2.5 µg/ml TTd in PBS) by overnight adsorption at 4° C. 1% (w/v) BSA/PBS were applied as a blocking reagent for 2 h at room temperature. This blocking step, as well as all subsequent ELISA steps, were followed by a wash with 0.05% (v/v) Tween 20 in PBS (four times, 200 µl/well). Appropriately diluted non-pooled serum (1:100) and tear (1:2) samples were incubated in the plates for 1 h at room temperature. Ag-specific antibody binding was detected with 1 h incubation at room temperature using biotin-labeled anti-mouse IgA antibody (BioLegend). Antigen-antibody interactions were visualized using the extrAvidin-peroxidase/o-phenylendiamine system (Sigma, Steinheim, Germany). Absorbance was recorded at 492/620 nm (A492/620). The cutoff value for each system were defined according to the A492/620 value obtained from "negative control" wells (1% BSA w/v in PBS as a sample) plus 3×SD. Samples were considered positive when the A492/620 value exceeded the cutoff value. (results are shown in FIG. 10)

TABLE 2

IgA levels in tears after immunization comparing different groups.

| immunization | IgA tears |
| --- | --- |
| TTd | 4.49 |
| TTd/wBP(whole cell Bord. Pert., wcBP) | 4.20 |
| TTd/chitosan | 4.78 |
| TTd/wBP/chitosan | 5.65 |
| wBP/chitosan | 1.16 |

TABLE 3

IgA levels in serum after immunization comparing different groups.

| immunization | IgA serum |
| --- | --- |
| TTd | 1.71 |
| TTd/wBP | 2.06 |
| TTd/chitosan | 2.58 |

TABLE 3-continued

IgA levels in serum after immunization comparing different groups.

| immunization | IgA serum |
| --- | --- |
| TTd/wBP/chitosan | 3.41 |
| wBP/chitosan | 1.05 |

The invention claimed is:

1. A method of treating a subject by active immunotherapy, comprising the steps of:
   providing a vaccine comprising a subunit vaccine antigen in an amount which is effective to provoke a protective immune response in the subject, chitosan, and an adjuvant, wherein the subunit vaccine antigen is tetanus toxoid (TTd) and wherein the adjuvant is whole cell *Bordetella pertussis* which has a particle size of >300 nm; and
   administering the vaccine to the subject onto the ocular surface in order to enhance a protective immune response on the ocular surface by inducing SIgA antibodies against the subunit vaccine antigen in the subject.

2. The method of claim 1, wherein the vaccine comprises at least two adjuvants.

3. The method of claim 1, wherein the vaccine administered to the subject comprises between 5 ng and 100 µg of the antigen.

4. The method of claim 2, wherein one of the adjuvants is a biodegradable polymeric microsphere.

5. The method of claim 1, wherein the antigen is conjugated to a carrier.

6. The method of claim 1, further comprising the step of administering an antiphlogistic agent.

7. The method of claim 1, wherein the subject is selected from the group consisting of humans, horses, birds, pigs, cattle, and rodents.

8. The method of claim 1, wherein the vaccine is administered as eye drops, an eye spray, an eye aerosol or an ocular ointment.

9. The method of claim 1, wherein the vaccine is administered to prevent a recurrence of ocular infections in the subject.

10. The method of claim 1, wherein the antigen and the adjuvant are administered simultaneously.

11. The method of claim 3, wherein the vaccine administered to the subject comprises between 500 ng and 50 µg of the antigen.

12. The method of claim 5, wherein the carrier and wherein the carrier is a biodegradable polymeric microsphere.

13. The method of claim 6, wherein the antiphlogistic agent is an anti-inflammatory agent.

14. The method of claim 13, wherein the antiphlogistic agent is azithromycin.

15. The method of claim 1, wherein the subject is a mammal.

* * * * *